United States Patent
Gebert-Schwarzwaelder et al.

(10) Patent No.: US 10,226,647 B2
(45) Date of Patent: *Mar. 12, 2019

(54) AGENTS FOR DYEING KERATIN FIBERS, CONTAINING AT LEAST ONE DIMERIC, DICATIONIC AZO DYE AND AT LEAST ONE ANIONIC SURFACTANT

(71) Applicant: Henkel AG & Co. KGaA, Duesseldorf (DE)

(72) Inventors: Antje Gebert-Schwarzwaelder, Neuss (DE); Helmut Giesa, Meerbusch (DE); Annika Koenen, Grevenbroich (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/528,538

(22) PCT Filed: Oct. 2, 2015

(86) PCT No.: PCT/EP2015/072773
§ 371 (c)(1),
(2) Date: May 22, 2017

(87) PCT Pub. No.: WO2016/082998
PCT Pub. Date: Jun. 2, 2016

(65) Prior Publication Data
US 2017/0266469 A1    Sep. 21, 2017

(30) Foreign Application Priority Data
Nov. 25, 2014 (DE) .................. 10 2014 223 939

(51) Int. Cl.
A61Q 5/10 (2006.01)
A61Q 5/06 (2006.01)
A61K 8/49 (2006.01)
A61K 8/36 (2006.01)
A61K 8/81 (2006.01)

(52) U.S. Cl.
CPC ............. *A61Q 5/065* (2013.01); *A61K 8/36* (2013.01); *A61K 8/49* (2013.01); *A61K 8/496* (2013.01); *A61K 8/4933* (2013.01); *A61K 8/4946* (2013.01); *A61K 8/8147* (2013.01)

(58) Field of Classification Search
CPC ...... A61Q 5/10; A61K 8/4933; A61K 8/8147; A61K 8/496; A61K 8/4946
See application file for complete search history.

(56) References Cited

U.S. PATENT DOCUMENTS

| 4,562,249 A | 12/1985 | Schwander et al. |
| 4,563,191 A | 1/1986 | Hahnke et al. |
| 4,607,071 A | 8/1986 | Haehnke et al. |
| 7,407,516 B2* | 8/2008 | Vidal .................... C09B 44/126 424/63 |
| 2001/0001333 A1 | 5/2001 | Samain |
| 2004/0200009 A1 | 10/2004 | Vidal |
| 2004/0244124 A1 | 12/2004 | Plos et al. |
| 2005/0235433 A1 | 10/2005 | Rondeau |
| 2006/0112502 A1 | 6/2006 | Cotteret et al. |
| 2012/0325261 A1* | 12/2012 | Hashimoto .............. A61Q 5/10 132/208 |
| 2014/0101868 A1 | 4/2014 | Hoffmann et al. |
| 2014/0165301 A1* | 6/2014 | Schweinsberg ........ A61K 8/898 8/409 |
| 2014/0289970 A1 | 10/2014 | Gross et al. |

FOREIGN PATENT DOCUMENTS

| CA | 2303209 A1 | 3/1999 |
| DE | 2822912 A1 | 11/1979 |
| DE | 4128490 A1 | 3/1993 |
| EP | 0531943 A1 | 3/1993 |
| EP | 1609456 A1 | 12/2005 |
| EP | 1483334 B1 | 7/2007 |
| EP | 1448156 B1 | 8/2007 |
| FR | 2915681 A1 | 11/2008 |
| GB | 910121 A | 11/1962 |
| GB | 1186753 A | 4/1970 |
| GB | 1189753 A | 4/1970 |
| WO | 02100369 A2 | 12/2002 |

OTHER PUBLICATIONS

STIC Search Report dated Jul. 2, 2017.*
EPO, International Search Report and Written Opinion issued in International Application PCT/EP2015/072773, dated Nov. 12, 2015.
EPO, International Search Report and Written Opinion issued in International Application No. PCT/EP2015/073779 dated Nov. 30, 2015.
Preliminary Amendment for U.S. Application entitled "Agents for Dyeing Keratin Fibres, Containing at Least One Dimeric, Dicationic Azo Dye With Special Substitution Pattern".
Substitute Specification for U.S. Application entitled "Agents for Dyeing Keratin Fibres, Containing at Least One Dimeric, Dicationic Azo Dye With Special Substitution Pattern".
EPO, International Search Report and Written Opinion issued in International Application PCT/EP2015/073775, dated Dec. 1, 2015.
Preliminary Amendment for U.S. Application entitled "Agents for Dyeing Keratin Fibers, Containing at Least One Dimeric, Dicationic Azo Dye and at Least One Anionic and/or Cationic Surfactant".
Substitute Specification for U.S. Application entitled "Agents for Dyeing Keratin Fibers, Containing at Least One Dimeric, Dicationic Azo Dye and at Least One Anionic and/or Cationic Surfactant".
EPO, International Search Report and Written Opinion issued in International Application No. PCT/EP2015/073776 dated Nov. 30, 2015.
Preliminary Amendment for U.S. Application entitled "Agents for Dyeing Keratin Fibers, Containing at Least One Dimeric, Ring-Bridged Azo Dye".
Substitute Specification for U.S. Application entitled "Agents for Dyeing Keratin Fibers, Containing at Least One Dimeric, Ring-Bridged Azo Dye".

(Continued)

Primary Examiner — Eisa B Elhilo
(74) Attorney, Agent, or Firm — Lorenz & Kopf, LLP

(57) ABSTRACT

The present disclosure relates to agents for dyeing keratin fibers, in particular human hair, containing, in a cosmetic carrier, (a) at least one direct dye of formula (I), and (b) at least one anionic surfactant.

8 Claims, No Drawings

(56) References Cited

OTHER PUBLICATIONS

EPO, International Search Report and Written Opinion issued in International Application PCT/EP2015/073776, dated Nov. 30, 2015.
USPTO, Office Action in U.S. Appl. No. 15/528,529 dated Aug. 31, 2017.
USPTO, Office Action in U.S. Appl. No. 15/528,539 dated Aug. 31, 2017.
USPTO, Office Action in U.S. Appl. No. 15/528,530 dated Aug. 31, 2017.
USPTO, Office Action in U.S. Appl. No. 15/528,532 dated Aug. 31, 2017.
STIC Search Report dated Jul. 29, 2017 (U.S. Appl. No. 15/528,529).
STIC Search Report dated Aug. 6, 2017 (U.S. Appl. No. 15/528,539).
STIC Search Report dated Aug. 1, 2017 (U.S. Appl. No. 15/528,530).
STIC Search Report dated Jun. 28, 2017 (U.S. Appl. No. 15/528,532).

\* cited by examiner

AGENTS FOR DYEING KERATIN FIBERS, CONTAINING AT LEAST ONE DIMERIC, DICATIONIC AZO DYE AND AT LEAST ONE ANIONIC SURFACTANT

CROSS-REFERENCE TO RELATED APPLICATION

This application is a U.S. National-Stage entry under 35 U.S.C. § 371 based on International Application No. PCT/EP2015/072773, filed Oct. 2, 2015 which was published under PCT Article 21(2) and which claims priority to German Application No. 10 2014 223 939.7, filed Nov. 25, 2014, which are all hereby incorporated in their entirety by reference.

TECHNICAL FIELD

This application pertains to agents for dyeing keratin fibers, in particular human hair, which contain (a) at least one dimeric, dicationic azo dye of a specific formula (I) in combination with (b) at least one anionic surfactant.

BACKGROUND

It has been found that the color intensity of cationic azo dyes, in particular of the specific azo dyes of formula (I), can be increased by use of specific anionic surfactants (b). A further subject of the present disclosure is therefore the use of anionic surfactants (b) for improving the color absorption capability of cationic azo dyes, in particular of the specific azo dyes of formula (I), on keratin fibers.

Generally, either direct dyes or oxidation dyes are used for the dyeing of keratin fibers. Intense colorings having good fastness properties can indeed be attained with oxidation dyes, however the color generally develops under the influence of oxidizing agents, such as $H_2O_2$, which in some cases can result in damage to the fibers. In addition, some oxidation dye precursors or specific mixtures of oxidation dye precursors can have a sensitizing effect in individuals who have sensitive skin. Direct dyes are applied under more gentle conditions. However, the disadvantage of these dyes lies in the fact that the colorings often have only insufficient fastness properties.

Depending on the desired color result, a person skilled in the art will use direct dyes of different dye classes. The direct dyes known from the prior art for example belong to the class of nitro dyes, anthraquinone dyes, azo dyes, triarylmethane dyes, or methine dyes. All of these dye classes should meet a specific requirement profile for use in the field of cosmetics. Direct dyes should thus deliver an intense color result and should have the best possible fastness properties. The color result obtained with direct dyes should be influenced as little as possible by ambient influences, i.e. the dyes should have a good fastness to washing, fastness to light, and fastness to rubbing, for example. Chemical influences to which the keratin fibers can be exposed after the coloring process (such as permanent waving) should change the color result to the smallest extent possible.

So as to also at the same time achieve a lightening with the dyeing, the direct dyes where possible should also be compatible with and stable in respect to the oxidizing agents (such as hydrogen peroxide and/or persulfates) usually used in the bleaching process.

Cationic azo dyes have proven to be a dye class having an excellent requirements profile. Azo dyes are generally characterized by a high stability. In addition, on account of their positive charge, cationic azo dyes have a high affinity to the keratin fiber, which is negatively charged to a greater or lesser extent.

If keratin fibers are to be oxidatively lightened or bleached, direct dyes can also be used in combination with oxidizing agents. Aqueous hydrogen peroxide solutions are generally applied to the keratin fibers for the bleaching of hair either alone or in combination with further oxidizing agents acting as bleach activators, such as persulfate salts. In order to attain a sufficient bleaching effect, agents of this type are usually set to be heavily alkaline, with the pH value here generally lying between 9 and 10.5. Melanin, i.e. the natural, color-giving pigments of the hair fibers, is oxidatively destroyed by the action of the oxidizing agents, and a decolorization or lightening of the fibers is achieved in this way. The melanin is localized in the cortex of the hair fibers and can be divided into two pigments classes. Eumelanins are the first, brown-black pigment class, whereas the reddish pigments richer in sulfur are referred to as pheomelanins. Due to the different resistances of the various pigment types with respect to oxidizing agents, however, the pheomelanins and eumelanins are not always decolorized uniformly. In addition, in darker hair having a high melanin content, the melanin can only be broken down in part or incompletely, such that a residual amount of the color-giving pigments remains in the hair after the bleaching. In these cases, the residual content of the melanin still present in the hair after the oxidative process leads to a yellowish to reddish nuance shift. When bleaching darker hair in particular, there is thus a color shift in the direction of warm (reddish) tones.

Such color shifts in the direction of warm tones are usually undesired by the user. This color shift is therefore usually counteracted by a tinting in the corresponding complementary color. Here, the objective is to achieve a silvery cooler impression of the bleach result. A person skilled in the art refers to a "matting" in this context.

For the matting of orangeish shades of blonde, blue direct dyes can be used in particular. For the most complete weakening possible of the orange color impression, it is advantageous here if the blue dye itself does not have any red component in its coloring. Dyes in pure blue tones are thus better, compared to purplish-blue dyes, for the matting of a bleaching result that is too orange.

Within the group of direct blue dyes that can be used in market products, there are only very few representatives which allow coloring in pure blue shades without red component. No dyes which meet all of the aforementioned preconditions in an optimal manner are known from the prior art. There is also a great demand for stable dyes which color the keratin fibers in pure blue shades and which deliver an intense color result with excellent fastness properties.

Monomeric cationic azo dyes that have long been known from the prior art are for example the representatives constituted by Basic Orange 31 (alternative name: 2-[(4-aminophenyl)azo]-1,3-dimethyl-1H-imidazolium chloride, CAS-Nr. 97404-02-9) and Basic Red 51 (alternative name: 2-[((4-dimethylamino)phenyl)azo]-1,3-dimethyl-1H-imidazolium chloride, CAS-Nr. 77061-58-6).

Both dyes color keratin fibers with excellent color intensity in the orange to red nuance range. There is additionally still also a need for direct blue dyes which are compatible in an optimal manner with these two dyes.

BRIEF SUMMARY

Agents for dyeing keratin fibers and methods for improving the color absorption capability of cationic azo dyes onto keratin fibers are provided herein. In an exemplary embodiment, an agent for dyeing keratin fibers includes, in a cosmetic carrier, a) at least one direct dye of formula (I),

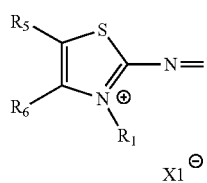
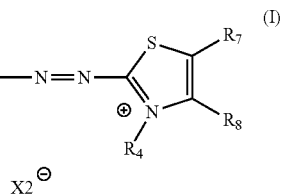

wherein

R1, R4 independently of one another stand for a $C_1$-$C_6$ alkyl group, a $C_2$-$C_6$ alkenyl group, a hydroxy $C_2$-$C_6$ alkyl group, a cyano $C_1$-$C_6$ alkyl group, a halogen $C_1$-$C_6$ alkyl group, an aryl $C_1$-$C_6$ alkyl group, a heteroaryl $C_1$-$C_6$ alkyl group, an aryl group, or a heteroaryl group, R2, R3 independently of one another stand for a hydrogen atom, a $C_1$-$C_6$ alkyl group, a $C_2$-$C_6$ alkenyl group, a hydroxy $C_2$-$C_6$ alkyl group, a cyano $C_1$-$C_6$ alkyl group, a halogen $C_1$-$C_6$ alkyl group, an aryl $C_1$-$C_6$ alkyl group, a heteroaryl $C_1$-$C_6$ alkyl group, an aryl group, or a heteroaryl group.

R5, R6, R7, R8 independently of one another stand for a hydrogen atom, a $C_1$-$C_6$ alkyl group, a halogen atom from the group of chlorine, bromine, fluorine or iodine, or for a $C_1$-$C_6$ alkoxy group, X1, X2 independently of one another stand for a physiologically acceptable anion, chloride, bromide, iodide, methyl sulfate, methyl sulfonate, p-toluene sulfonate, acetate, hydrogen sulfate, ½ sulfate, or ½ tetrachlorozincate, Q stands for a grouping of formula (II), (III), (IV), or (V),

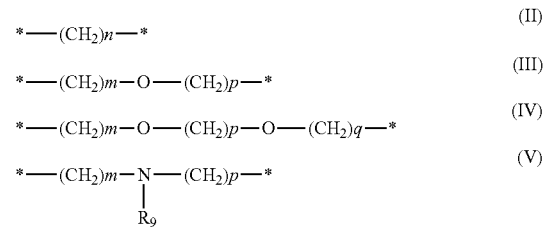

n stands for an integer of from 3 to 6, m, p, q each stand, independently of one another, for the numbers 2 or 3, R9 stands for a hydrogen atom, for a $C_1$-$C_6$ alkyl group, a $C_2$-$C_6$ alkenyl group, or for a hydroxy $C_2$-$C_6$ alkyl group, and (b) at least one anionic surfactant.

In another exemplary embodiment, a method for improving the color absorption capability of cationic azo dyes onto keratin fibers is provided. The method includes using one or more anionic surfactants (b) of formula (B1)

$$R-O-(CH_2-CH_2O)_x-CH_2-COOM \quad \text{(B1)}$$

wherein

R stands for a linear alkyl group having 8 to 30 C atoms, x stands for an integer from 0 to 16, M stands for hydrogen, a metal, an alkali metal, sodium, potassium, lithium, an alkaline earth metal, ½ magnesium, ½ calcium, ½ zinc, or an ammonium ion ($NH_4^+$), for improving the color absorption capability of cationic azo dyes onto keratin fibers.

DETAILED DESCRIPTION

The following detailed description is merely exemplary in nature and is not intended to limit the present disclosure or the application and uses of the subject matter as described herein. Furthermore, there is no intention to be bound by any theory presented in the preceding background or the following detailed description.

The object of various embodiments of the present disclosure was therefore to find new matting dyes which meet the usual fastness requirements placed on direct dyes and which make it possible to color keratin fibers in a pure blue tone without red component. The colorings attainable with these dyes should have a particularly high color intensity.

In addition, the aforementioned blue dyes should also be particularly compatible with the cationic azo dyes Basic Orange 31 and Basic Red 51.

Surprisingly, it has now been possible to find that this object is achieved to an outstanding extent if dyes of the formula (I) described hereinafter are used in combination with at least one anionic surfactant in agents for dyeing keratin fibers.

A first subject matter of the present disclosure is an agent for dyeing keratin fibers, in particular human hair, containing in a cosmetic carrier (a) at least one direct dye of formula (I),

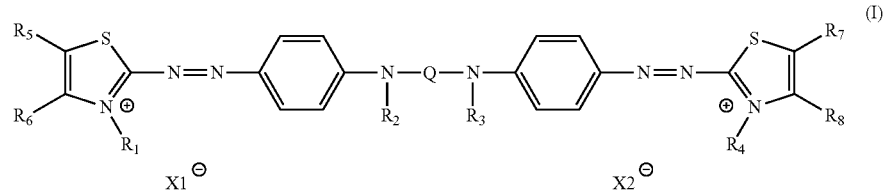

wherein

R1, R4 independently of one another stand for a $C_1$-$C_6$ alkyl group, a $C_2$-$C_6$ alkenyl group, a hydroxy $C_2$-$C_6$ alkyl group, a cyano $C_1$-$C_6$ alkyl group, a halogen $C_1$-$C_6$ alkyl group, an aryl $C_1$-$C_6$ alkyl group, a heteroaryl $C_1$-$C_6$ alkyl group, an aryl group, or a heteroaryl group, R2, R3 independently of one another stand for a hydrogen atom, a $C_1$-$C_6$ alkyl group, a $C_2$-$C_6$ alkenyl group, a hydroxy $C_2$-$C_6$ alkyl group, a cyano $C_1$-$C_6$ alkyl group, a halogen $C_1$-$C_6$ alkyl group, an aryl $C_1$-$C_6$ alkyl group, a heteroaryl $C_1$-$C_6$ alkyl group, an aryl group, or a heteroaryl group.

R5, R6, R7, R8 independently of one another stand for a hydrogen atom, a $C_1$-$C_6$ alkyl group, a halogen atom from the group of chlorine, bromine, fluorine or iodine, or for a $C_1$-$C_6$ alkoxy group, X1, X2 independently of one another stand for a physiologically acceptable anion, preferably from the group of chloride, bromide, iodide, methyl sulfate, methyl sulfonate, p-toluene sulfonate, acetate, hydrogen sulfate, ½ sulfate, or ½ tetrachlorozincate, Q stands for a grouping of formula (II), (III), (IV) or (V),

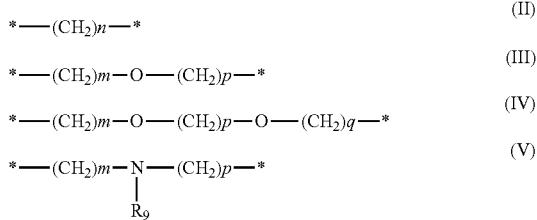

n stands for an integer of from 3 to 6, m, p, q each stand, independently of one another, for the numbers 2 or 3, R9 stands for a hydrogen atom, for a $C_1$-$C_6$ alkyl group, a $C_2$-$C_6$ alkenyl group, or for a hydroxy $C_2$-$C_6$ alkyl group, and (b) at least one anionic surfactant.

Keratinic fibers, keratin-containing fibers, or keratin fibers are understood to mean furs, wool, feathers and in particular human hair. Although the agents according to embodiments of the present disclosure are suitable primarily for the lightening of keratin fibers, there is in principle nothing against a use also in other areas.

The term "dyeing of keratin fibers" as used in accordance with the present disclosure includes any form of a color change to the fibers. In particular, the color changes included under the terms tinting, bleaching, matting, oxidative dyeing, semi-permanent dyeing, permanent dyeing and temporary dyeing are included. Color changes that have a lighter color result compared to the starting color, such as dyeing processes with a bleaching effect, are also explicitly included in accordance with the present disclosure. The term "matting of keratin fibers" is understood to mean the counteraction of undesirable nuance shifts which occur in the case of oxidative color changes of keratin fibers, in particular in the case of lightening or bleaching processes. The objective of matting is to weaken the orange to reddish color impression caused by incomplete bleaching and to produce a silvery cool color perception after the bleaching process. The active substances used in the case of matting can be applied in the form of a post-treatment step after the lightening or bleaching of the keratin fibers. However, it is also possible to apply the active substances used for the matting within the scope of a one-step process together with the bleaching agent to the keratin fibers. direct dyes either alone or in a dye mixture having the suitable color properties can be used as active substances suitable for the matting. In addition, it is also possible to use direct dyes in combination with oxidation dye precursors (developers and couplers) for the matting.

The agents according to an embodiment of the present disclosure contain the direct dyes of formula (I) in a cosmetic carrier. This cosmetic carrier is preferably aqueous, alcoholic, or aqueous-alcoholic. For the purpose of the hair treatment, such carriers are, for example, creams, emulsions, gels, or also surfactant-containing foaming solutions, for example shampoos, foam aerosols, or other preparations which are suitable for use on the hair. However, it is also possible to provide a powdery or also tablet-like formulation for storage. This is then mixed prior to use in an aqueous solvent or with organic solvents or with mixtures of water and organic solvents so as to obtain a ready-to-use mixture. An aqueous carrier in the sense of the present disclosure contains at least about 40% by weight, in particular at least about 50% by weight, of water. Aqueous-alcoholic carriers in the sense of the present disclosure are understood to be water-containing compositions containing about 3 to about 70% by weight of a $C_1$-$C_4$ alcohol, in particular ethanol or isopropanol. The agents according to an exemplary embodiment of the present disclosure can additionally contain further organic solvents, such as 4-methoxybutanol, ethyldiglycol, 1,2-propylene glycol, n-propanol, n-butanol, n-butylene glycol, glycerol, diethylene glycol monoethyl ether, and diethylene glycol mono-n-butyl ether. Here, all water-soluble organic solvents are preferred. Preferred agents according to an exemplary embodiment of the present disclosure are characterized in that they additionally contain a non-aqueous solvent, wherein preferred agents according to the embodiment contain the solvent in a concentration of about 0.1 to about 30% by weight, preferably in a concentration of about 1 to about 20% by weight, very particularly preferably in a concentration of about 2 to about 10% by weight, in each case in relation to the agent.

The agents according to an exemplary embodiment of the present disclosure contain, as first essential ingredient (a), at least one dye of formula (I).

The substituents R1 to R9 of the compounds of formula (I) are explained hereinafter by way of example: Examples of a $C_1$-$C_6$ alkyl group are the groups methyl, ethyl, propyl, isopropyl, n-butyl, s-butyl and t-butyl, n-pentyl and n-hexyl. Propyl, ethyl and methyl are preferred alkyl groups. Examples of a $C_2$-$C_6$ alkenyl group are vinyl, allyl, but-2-enyl, but-3-enyl and isobutenyl, preferred $C_2$-$C_6$ alkenyl groups are vinyl and allyl. Preferred examples of a hydroxy $C_1$-$C_6$ alkyl group are a hydroxymethyl group, a 2-hydroxyethyl group, a 2-hydroxypropyl group, a 3-hydroxypropyl group, a 4-hydroxybutyl group, a 5-hydroxypentyl group and a 6-hydroxyhexyl group; a 2-hydroxyethyl group is particularly preferred. Preferred examples of cyano $C_1$-$C_6$ alkyl groups are the cyanomethyl group, the 2-cyanoethyl group and the 3-cyanopropyl group. Halogen $C_1$-$C_6$ alkyl groups that are preferred in accordance with the present disclosure are the chloromethyl group, the bromomethyl group, the fluoromethyl group, the 2-chloroethyl group, the 2-bromoethyl group, the 2-fluoromethyl group, the 2-chloropropyl group, the 2-bromopropyl group, the 2-fluoropropyl group, the 3-chloropropyl group, the 3-bromopropyl group and the 3-fluoropropyl group. Preferred examples of aryl $C_1$-$C_6$ alkyl groups are benzyl, 1-phenethyl and 2-phenylethyl. Examples of heteroaryl $C_1$-$C_6$ alkyl groups include the imidazol-1-ylmethyl group, the imidazol-2-ylmethyl group, the imidazol-4-ylmethyl group, the pyridin-2-yl group, the pyridin-3-yl group and the pyridin-4-ylmethyl group. Aryl groups that are preferred in accordance with the present disclosure are the phenyl group and the naphthyl group. Examples of a heteroaryl group are the pyridin-2-yl group, the pyridin-3-yl group, the pyridin-4-yl group, the imidazol-1-yl group, the imidazol-2-yl group and the imidazol-4-yl group. Halogen atoms are selected from the group of chlorine, bromine, fluorine and/or iodine, with chlorine and bromine being particularly preferred here. Examples of a $C_1$-$C_6$ alkoxy group include the methoxy group, the ethoxy group, and the propoxy group.

The compounds of general formula (I) carry the groups R1 and R4 in each case at the nitrogen atom of the two thiazole rings. Here, R1 and R4 can be the same or different.

The groups R1 and R4 are preferably the same. R1 and R4 preferably stand independently of one another for a C1-C6 alkyl group or for a C2-C6 alkenyl group. R1 and R4 particularly preferably stand independently of one another for a C1-C6 alkyl group, in particular for a methyl group or for an ethyl group.

The compounds of general formula (I) also carry the groups R2 and R3; here, R2 and R3 can be the same or different. The groups R2 and R3 are preferably the same.

R2 and R3 preferably stand independently of one another for a hydrogen atom, a $C_1$-$C_6$ alkyl group or a $C_2$-$C_6$ alkenyl group.

R2 and R3 particularly preferably stand independently of one another for a hydrogen atom or a C1-C6 alkyl group. R2 and R3 particularly preferably stand independently of one another for a hydrogen atom, a methyl group, or an ethyl group.

Furthermore, the compounds of general formula (I) also carry the groups R5, R6, R7 and R8; here, the groups R5 to R8 can be the same or different. The groups R5, R6, R7 and R8 preferably stand independently of one another for a hydrogen atom, a halogen atom, or a C1-C6 alkoxy group. The groups R5, R6, R7 and R8 particularly preferably all stand for a hydrogen atom.

In a particularly preferred embodiment an agent according to the present disclosure is characterized in that it contains (a) at least one direct dye of general formula (I), in which R1, R4 independently of one another stand for a $C_1$-$C_6$ alkyl group,
R2, R3 independently of one another stand for a hydrogen atom or for a $C_1$-$C_6$ alkyl group,
R5, R6, R7, R8 each stand for a hydrogen atom.

In a very particularly preferred embodiment an agent according to the present disclosure is characterized in that it contains (a) at least one direct dye of general formula (I), in which
R1, R4 independently of one another stand for a methyl group or for an ethyl group,
R2, R3 independently of one another stand for a hydrogen atom, for a methyl group, or for an ethyl group, and
R5, R6, R7, R8 each stand for a hydrogen atom.

The dyes of formula (I) according to an exemplary embodiment of the present disclosure are dimeric azo dyes which are doubly positively charge. The two positive charges are neutralized by the anionic counterions X1 and X2. Here, the dicationic organic part is responsible for the blue coloration of the keratin fibers. The counterions X1 and X2 serve merely to safeguard the electroneutrality, and therefore the exact nature of the counterions X1 and X2 does not play a key role for attaining the desired color result. Since the dye is used in a cosmetic agent, the counterions X1 and X2 must be physiologically compatible. In this context, physiologically compatible means suitable for use in the cosmetic agent (i.e. for use on human hair and on human skin). X1 and X2 are physiologically acceptable anions, preferably from the group of chloride, bromide, iodide, methyl sulfate, methyl sulfonate, p-toluene sulfonate, acetate, hydrogen sulfate, ½ sulfate, or ½ tetrachlorozincate.

Chloride is understood to mean an anion Cl⁻. Bromide is understood to mean an anion Br⁻. Iodide is understood to mean an anion J⁻. Methyl sulfate is understood to mean an anion $H_3COSO_4$—. The term p-toluene sulfonate is understood to mean an anion $H_3C(C_6H_4)SO_3$—. Acetate is understood to mean an anion $H_3CCOO^-$. Hydrogen sulfate is understood to mean an anion $HSO_4$—.

The term ½ sulfate is understood to mean a half equivalent of the doubly negatively charged anion SO42-. The term ½ tetrachlorozincate is understood to mean a half equivalent of the doubly negatively charged anion ZnCl42-. In the case of sulfate and tetrachlorozincate it is consequently also possible and also in accordance with the present disclosure if the dicationic dye of formula (I) is neutralized by an SO42-ion or by a ZnCl42-ion.

The grouping Q is a grouping which links the two singly positively charged chromophores, of the dye to the dicationic dimer. Q stands for a grouping of formula (II), (III), (IV) or (V),

(II)

(III)

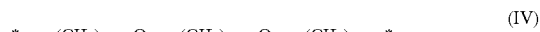

(IV)

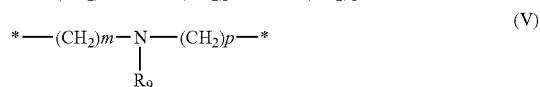

(V)

n stands for an integer from 3 to 6,
m, p, q each stand independently of one another for the numbers 2 or 3, and
R9 stands for a hydrogen atom, for a $C_1$-$C_6$ alkyl group, for a $C_2$-$C_6$ alkenyl group, or for a hydroxy $C_2$-$C_6$ alkyl group.

The two positions marked by a star each stand here for the linking positions to the two N atoms of formula (I).

In order to attain an intense color result, it has surprisingly proven to be fundamentally important and essential to the present disclosure that the linking grouping Q, which links the two individual chromophores to one another, has a chain length of at least 3 atoms.

For this reason, n in formula (II) stands for an integer of at least 3. The linking grouping Q of formula (II) therefore comprises at least 3 C atoms (i.e. in this case the grouping has the minimum length of —CH2-CH2-CH2-).

In the formula (III), m and p each stand for an integer of at least 2, and therefore this linking grouping in total has a chain length of at least 5 C and O atoms (i.e. in this case the grouping has a minimum length of —CH2-CH2-O—CH2-CH2-).

In the formula (IV) m, p and q each stand for an integer of at least 2, such that this linking grouping analogously has a chain length of at least 8 C and O atoms (i.e. in this case the grouping has a minimum length of —CH2-CH2-O—CH2-CH2-O—CH2-CH2-).

Analogously, in the formula (V) m and p also stand for integers of at least 2, and therefore this linking grouping also has a chain length of at least 5 C and N atoms.

Within the scope of comparative tests it has been found that dimeric azo dyes of the primary type of formula (I) which, however, have a linker group Q not according to an exemplary embodiment of the present disclosure with a length of just 2 C atoms have an extremely poor capability of absorbing color onto the keratin fibers.

Whereas intense colorings with a deeply dark-blue color tone could be attained with the dyes of formula (I) according to an exemplary embodiment of the present disclosure, colorings with analogous dimeric dyes which are linked via a shorter grouping Q with a chain length of just 2 C atoms led to practically no absorption of color at all onto the keratin fibers.

Without being limited to a theory, a rigid geometry associated with the short linker chain Q and a resultant unfavorable physical conformation of the dye might possibly impair the diffusion of the short-chain dimeric dyes into the keratin fibers.

Within the groupings Q of formulas (II), (III), (IV), and (V), the best color results and the most intense colorings could be attained with the grouping of formula (II).

In a very particularly preferred embodiment an agent according to the present disclosure is characterized in that it contains (a) at least one direct dye of general formula (I), in which Q stands for a grouping of formula (II)

$$*\!\!-\!\!(CH_2)_n\text{-}*  \qquad (II)$$

and n in each case independently of one another stands for an integer from 3 to 6.

In an explicitly very particularly preferred embodiment an agent according to the present disclosure is characterized in that it contains (a) at least one dye of general formula (I), in which Q stands for a grouping of formula (II), $$*\!\!-\!\!(CH_2)_n\text{-}*  \qquad (II)$$

and n stands for the number 3.

In a further preferred embodiment an agent for dyeing keratin fibers is characterized in that it contains at least one compound of general formula (I) which is selected from Salts of 3-methyl-2-[2-(4-{[3-({4-[2-(3-methyl-1,3-thiazol-3-ium-2-yl)diazen-1-yl]phenyl}amino)propyl]amino}phenyl)diazen-1-yl]-1,3-thiazol-3-ium

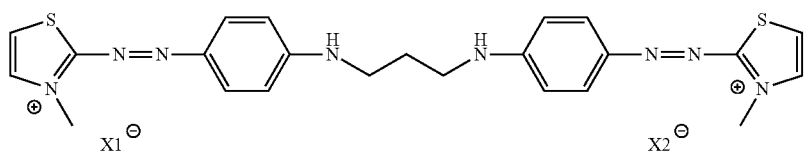

Salts of 3-methyl-2-[2-(4-{[4-({4-[2-(3-methyl-1,3-thiazol-3-ium-2-yl)diazen-1-yl]phenyl}amino)butyl]amino}phenyl)diazen-1-yl]-1,3-thiazol-3-ium

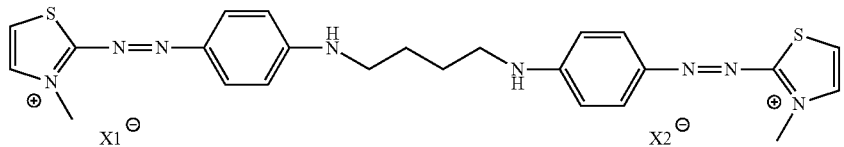

Salts of 3-methyl-2-[2-(4-{[5-({4-[2-(3-methyl-1,3-thiazol-3-ium-2-yl)diazen-1-yl]phenyl}amino)pentyl]amino}phenyl)diazen-1-yl]-1,3-thiazol-3-ium

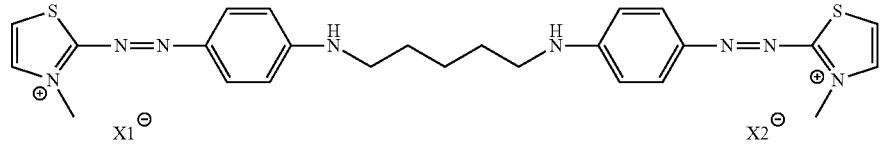

Salts of 3-methyl-2-(2-{4-[methyl({3-[methyl({4-[2-(3-methyl-1,3-thiazol-3-ium-2-yl)diazen-1-yl]phenyl})amino]propyl})amino]phenyl}diazen-1-yl)-1,3-thiazol-3-ium

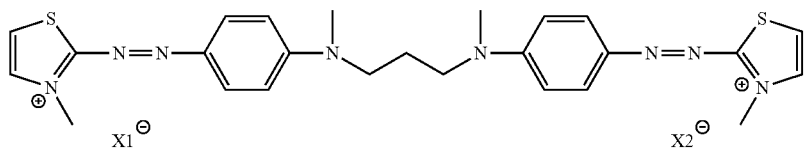

Salts of 3-methyl-2-(2-{4-[methyl({4-[methyl({4-[2-(3-methyl-1,3-thiazol-3-ium-2-yl)diazen-1-yl]phenyl})amino]butyl})amino]phenyl}diazen-1-yl)-1,3-thiazol-3-ium

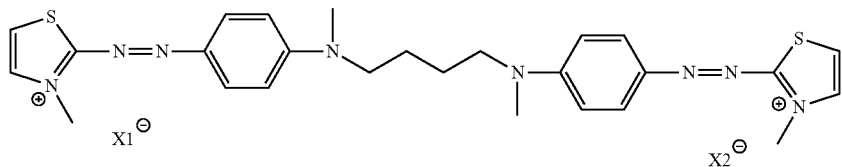

Salts of 3-methyl-2-(2-{4-[methyl({5-[methyl({4-[2-(3-methyl-1,3-thiazol-3-ium-2-yl)diazen-1-yl]phenyl})amino]pentyl})amino]phenyl}diazen-1-yl)-1,3-thiazol-3-ium

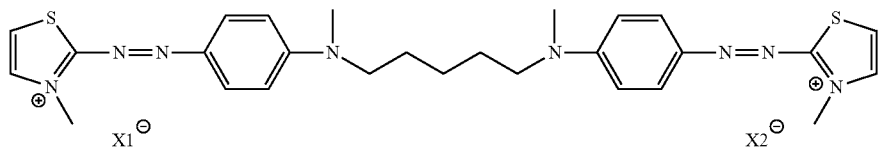

Salts of 2-(2-{4-[ethyl({3-[ethyl({4-[2-(3-methyl-1,3-thiazol-3-ium-2-yl)diazen-1-yl]phenyl})amino]propyl})amino]phenyl}diazen-1-yl)-3-methyl-1,3-thiazol-3-ium

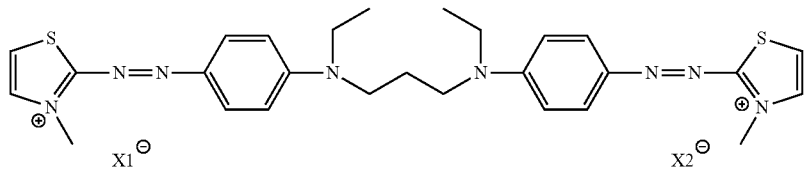

Salts of 2-(2-{4-[ethyl({4-[ethyl({4-[2-(3-methyl-1,3-thiazol-3-ium-2-yl)diazen-1-yl]phenyl})amino]butyl})amino]phenyl}diazen-1-yl)-3-methyl-1,3-thiazol-3-ium

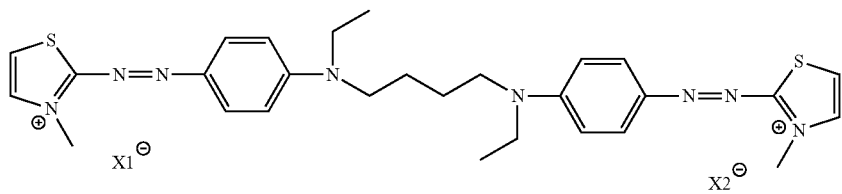

Salts of 2-(2-{4-[ethyl({5-[ethyl({4-[2-(3-methyl-1,3-thiazol-3-ium-2-yl)diazen-1-yl]phenyl})amino]pentyl})amino]phenyl}diazen-1-yl)-3-methyl-1,3-thiazol-3-ium

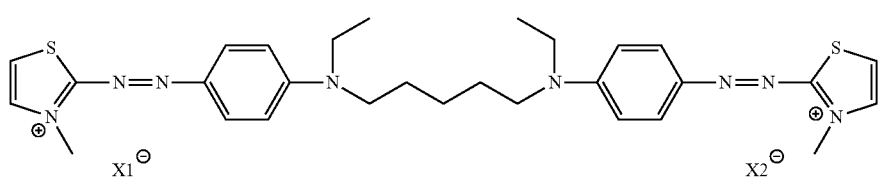

Salts of 3-ethyl-2-[2-(4-{[3-({4-[2-(3-ethyl-1,3-thiazol-3-ium-2-yl)diazen-1-yl]phenyl}amino)propyl]amino}phenyl)diazen-1-yl]-1,3-thiazol-3-ium

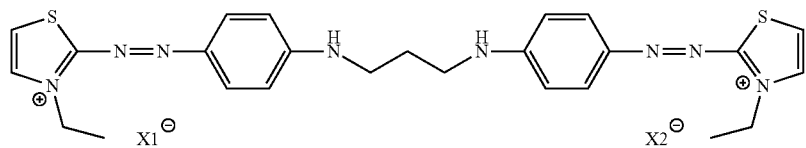

Salts of 3-ethyl-2-[2-(4-{[4-({4-[2-(3-ethyl-1,3-thiazol-3-ium-2-yl)diazen-1-yl]phenyl}amino)butyl]amino}phenyl)diazen-1-yl]-1,3-thiazol-3-ium

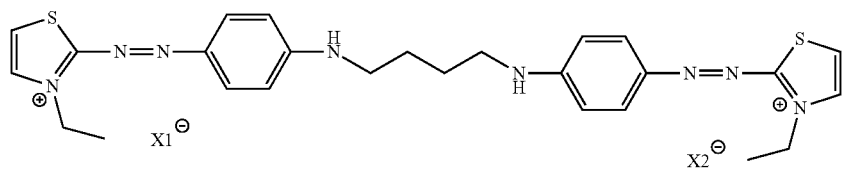

Salts of 3-ethyl-2-[2-(4-{[5-({4-[2-(3-ethyl-1,3-thiazol-3-ium-2-yl)diazen-1-yl]phenyl}amino)pentyl]amino}phenyl)diazen-1-yl]-1,3-thiazol-3-ium

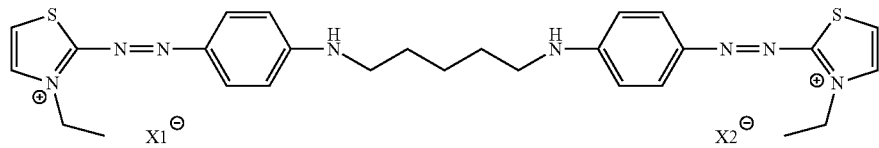

Salts of 3-ethyl-2-[2-(4-{[3-({4-[2-(3-ethyl-1,3-thiazol-3-ium-2-yl)diazen-1-yl]phenyl}(methyl)amino)propyl](methyl)amino}phenyl)diazen-1-yl]-1,3-thiazol-3-ium

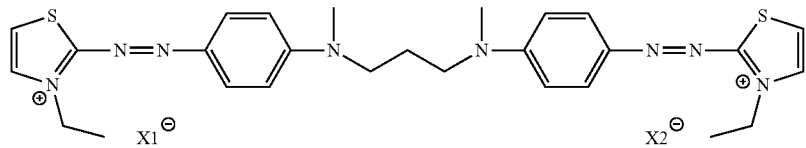

Salts of 3-ethyl-2-[2-(4-{[4-({4-[2-(3-ethyl-1,3-thiazol-3-ium-2-yl)diazen-1-yl]phenyl}(methyl)amino)butyl](methyl)amino}phenyl)diazen-1-yl]-1,3-thiazol-3-ium

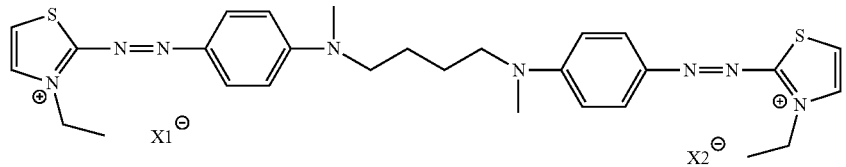

Salts of 3-ethyl-2-[2-(4-{[5-({4-[2-(3-ethyl-1,3-thiazol-3-ium-2-yl)diazen-1-yl]phenyl}(methyl)amino)pentyl](methyl)amino}phenyl)diazen-1-yl]-1,3-thiazol-3-ium

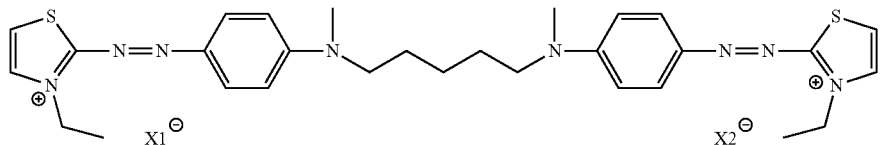

Salts of 3-ethyl-2-(2-{4-[ethyl({3-[ethyl({4-[2-(3-ethyl-1,3-thiazol-3-ium-2-yl)diazen-1-1]phenyl})amino]propyl})amino]phenyl}diazen-1-yl)-1,3-thiazol-3-ium

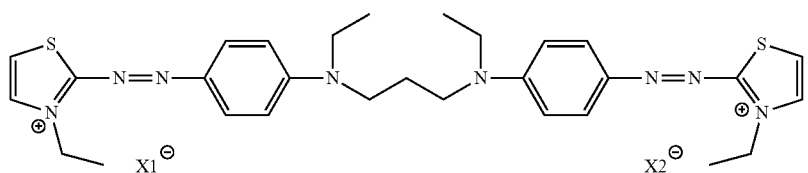

Salts of 3-ethyl-2-(2-{4-[ethyl({4-[ethyl({4-[2-(3-ethyl-1,3-thiazol-3-ium-2-yl)diazen-1-yl]phenyl})amino]butyl})amino]phenyl}diazen-1-yl)-1,3-thiazol-3-ium

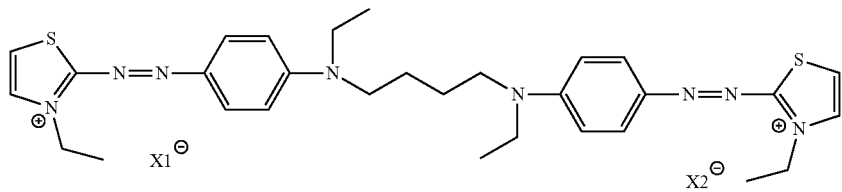

Salts of 3-ethyl-2-(2-{4-[ethyl({5-[ethyl({4-[2-(3-ethyl-1,3-thiazol-3-ium-2-yl)diazen-1-yl]phenyl})amino]pentyl})amino]phenyl}diazen-1-yl)-1,3-thiazol-3-ium

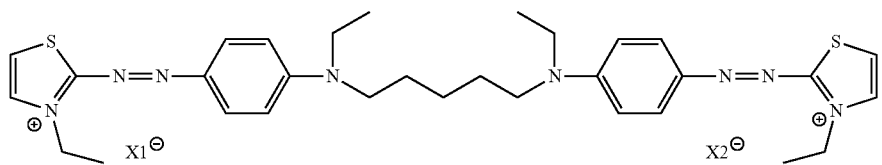

Salts of 3-methyl-2-{2-[4-({2-[2-({4-[2-(3-methyl-1,3-thiazol-3-ium-2-yl)diazen-1-yl]phenyl}amino)ethoxy]ethyl}amino)phenyl]diazen-1-yl}-1,3-thiazol-3-ium

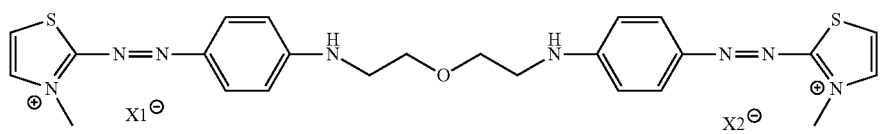 [SMILES: C[n+]1ccsc1N=Nc1ccc(NCCOCCNc2ccc(N=Nc3scc[n+]3C)cc2)cc1 ; "X1" ; "X2"]

Salts of 3-methyl-2-(2-{4-[methyl(2-{2-[methyl({4-[2-(3-methyl-1,3-thiazol-3-ium-2-yl)diazen-1-yl]phenyl})amino]ethoxy}ethyl)amino]phenyl}diazen-1-yl)-1,3-thiazol-3-ium

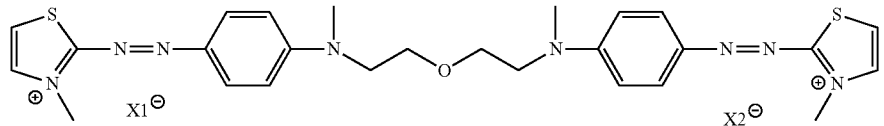 [SMILES: CN(CCOCCN(C)c1ccc(N=Nc2scc[n+]2C)cc1)c1ccc(N=Nc2scc[n+]2C)cc1 ; "X1" ; "X2"]

Salts of 2-(2-{4-[ethyl(2-{2-[ethyl({4-[2-(3-methyl-1,3-thiazol-3-ium-2-yl)diazen-1-yl]phenyl})amino]ethoxy}ethyl)amino]phenyl}diazen-1-yl)-3-methyl-1,3-thiazol-3-ium

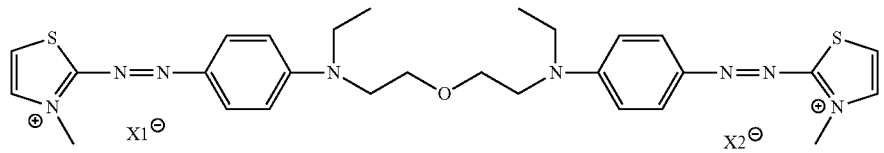 [SMILES: CCN(CCOCCN(CC)c1ccc(N=Nc2scc[n+]2C)cc1)c1ccc(N=Nc2scc[n+]2C)cc1 ; "X1" ; "X2"]

Salts of 3-ethyl-2-{2-[4-({2-[2-({4-[2-(3-ethyl-1,3-thiazol-3-ium-2-yl)diazen-1-yl]phenyl}amino)ethoxy]ethyl}amino)phenyl]diazen-1-yl}-1,3-thiazol-3-ium

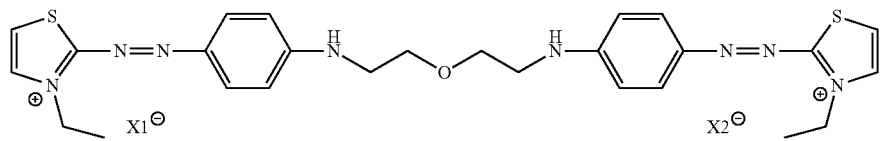

Salts of 3-ethyl-2-{2-[4-({2-[2-({4-[2-(3-ethyl-1,3-thiazol-3-ium-2-yl)diazen-1-yl]phenyl}(methyl)amino)ethoxy]ethyl}(methyl)amino)phenyl]diazen-1-yl}-1,3-thiazol-3-ium

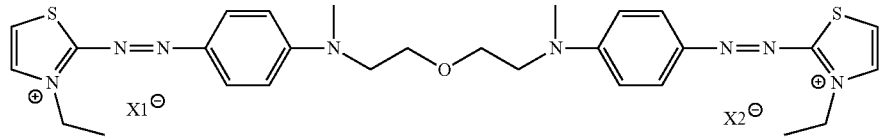

Salts of 3-ethyl-2-(2-{4-[ethyl(2-{2-[ethyl({4-[2-(3-ethyl-1,3-thiazol-3-ium-2-yl)diazen-1-yl]phenyl}amino]ethoxy}ethyl)amino]phenyl}diazen-1-yl)-1,3-thiazol-3-ium

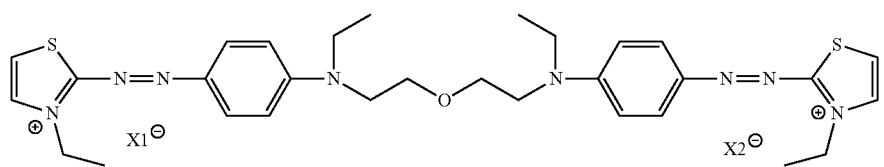

Salts of 3-methyl-2-{2-[4-(10-{4-[2-(3-methyl-1,3-thiazol-3-ium-2-yl)diazen-1-yl]phenyl}-4J-dioxa-1,10-diazadecan-1-yl)phenyl]diazen-1-yl}-1,3-thiazol-3-ium

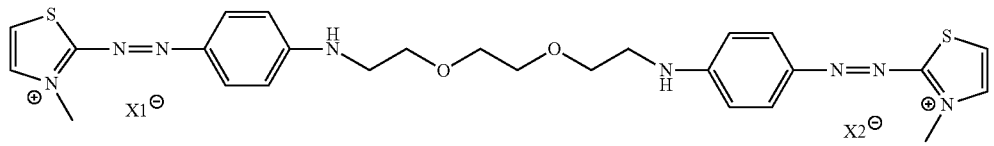 [SMILES: C[n+]1ccsc1N=Nc1ccc(NCCOCCOCCNc2ccc(N=Nc3scc[n+]3C)cc2)cc1 ; "X1" ; "X2"]

Salts of 3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium

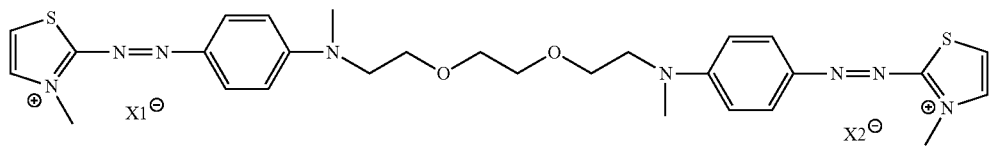 [SMILES: CN(CCOCCOCCN(C)c1ccc(N=Nc2scc[n+]2C)cc1)c1ccc(N=Nc2scc[n+]2C)cc1 ; "X1" ; "X2"]

Salts of 3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium

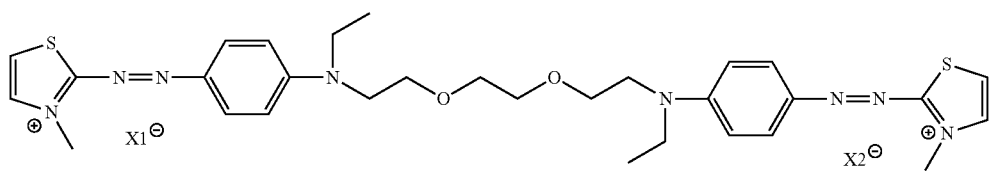 [SMILES: CCN(CCOCCOCCN(CC)c1ccc(N=Nc2scc[n+]2C)cc1)c1ccc(N=Nc2scc[n+]2C)cc1 ; "X1" ; "X2"]

Salts of 3-ethyl-2-{2-[4-(10-{4-[2-(3-ethyl-1,3-thiazol-3-ium-2-yl)diazen-1-yl]phenyl}-4J-dioxa-1,10-diazadecan-1-yl)phenyl]diazen-1-yl}-1,3-thiazol-3-ium

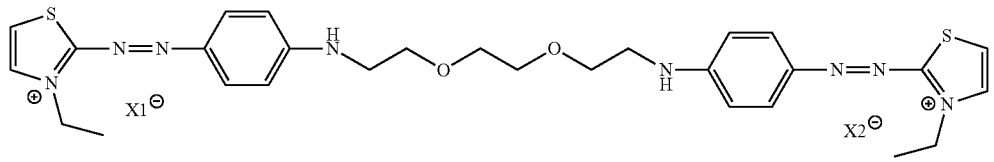

Salts of 3-ethyl-2-{2-[4-(11-{4-[2-(3-ethyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium

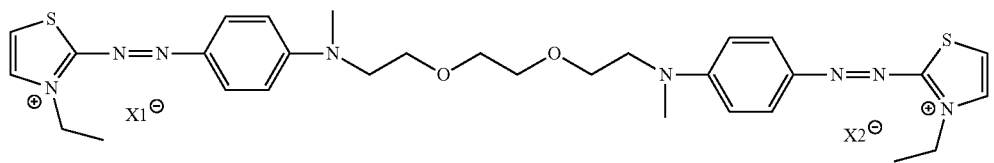

Salts of 3-ethyl-2-{2-[4-(12-{4-[2-(3-ethyl-1,3-thi-azol-3-ium-2-yl)diazen-1-yl]phenyl}-6,9-dioxa-3,12-diazatetradecan-3-yl)phenyl]diazen-1-yl}-1,3-thi-azol-3-ium

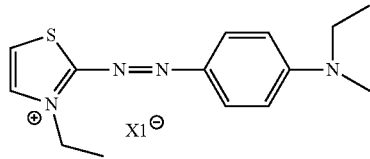
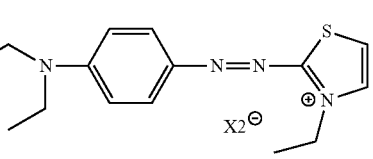

The aforementioned compounds are dicationic dimeric dyes, wherein the organic dictation is neutralized by the two anions X1 and X2. The anions X1 and X2 can each be a physiologically acceptable anion, preferably from the group of chloride, bromide, iodide, methyl sulfate, methyl sulfonate, p-toluene sulfonate, acetate, hydrogen sulfate, ½ sulfate, or ½ tetrachlorozincate.

In a particularly preferred embodiment, an agent according to the present disclosure for dyeing keratin fibers is characterized in that it contains, as dye of formula (a), at least one compound selected from the group consisting of 3-methyl-2-[2-(4-{[3-({4-[2-(3-methyl-1,3-thiazol-3-ium-2-yl)diazen-1yl]phenyl}amino)propyl]amino}phenyl)di-azen-1-yl]-1,3-thiazol-3-ium dichloride 3-methyl-2-[2-(4-{[3-({4-[2-(3-methyl-1,3-thiazol-3-ium-2-yl)diazen-1yl]phenyl}amino)propyl]amino}phenyl)di-azen-1-yl]-1,3-thiazol-3-ium dibromide 3-methyl-2-[2-(4-{[3-({4-[2-(3-methyl-1,3-thiazol-3-ium-2-yl)diazen-1yl]phenyl}amino)propyl]amino}phenyl)di-azen-1-yl]-1,3-thiazol-3-ium sulfate 3-methyl-2-[2-(4-{[3-({4-[2-(3-methyl-1,3-thiazol-3-ium-2-yl)diazen-1yl]phenyl}amino)propyl]amino}phenyl)di-azen-1-yl]-1,3-thiazol-3-ium di(toluenesulfonate)

3-methyl-2-[2-(4-{[3-({4-[2-(3-methyl-1,3-thiazol-3-ium-2-yl)diazen-1yl]phenyl}amino)propyl]amino}phenyl)di-azen-1-yl]-1,3-thiazol-3-ium di(methyl sulfate)

3-methyl-2-[2-(4-{[3-({4-[2-(3-methyl-1,3-thiazol-3-ium-2-yl)diazen-1yl]phenyl}amino)propyl]amino}phenyl)di-azen-1-yl]-1,3-thiazol-3-ium tetrachlorozincate 3-methyl-2-[2-(4-{[4-({4-[2-(3-methyl-1,3-thiazol-3-ium-2-yl)diazen-1yl]phenyl}amino)butyl]amino}phenyl)di-azen-1-yl]-1,3-thiazol-3-ium dichloride 3-methyl-2-[2-(4-{[4-({4-[2-(3-methyl-1,3-thiazol-3-ium-2-yl)diazen-1yl]phenyl}amino)butyl]amino}phenyl)di-azen-1-yl]-1,3-thiazol-3-ium dibromide 3-methyl-2-[2-(4-{[4-({4-[2-(3-methyl-1,3-thiazol-3-ium-2-yl)diazen-1yl]phenyl}amino)butyl]amino}phenyl)di-azen-1-yl]-1,3-thiazol-3-ium sulfate 3-methyl-2-[2-(4-{[4-({4-[2-(3-methyl-1,3-thiazol-3-ium-2-yl)diazen-1yl]phenyl}amino)butyl]amino}phenyl)di-azen-1-yl]-1,3-thiazol-3-ium di(toluenesulfonate)

3-methyl-2-[2-(4-{[4-({4-[2-(3-methyl-1,3-thiazol-3-ium-2-yl)diazen-1yl]phenyl}amino)butyl]amino}phenyl)di-azen-1-yl]-1,3-thiazol-3-ium di(methyl sulfate)

3-methyl-2-[2-(4-{[4-({4-[2-(3-methyl-1,3-thiazol-3-ium-2-yl)diazen-1yl]phenyl}amino)butyl]amino}phenyl)di-azen-1-yl]-1,3-thiazol-3-ium tetrachlorozincate 3-methyl-2-[2-(4-{[5-({4-[2-(3-methyl-1,3-thiazol-3-ium-2-yl)diazen-1-yl]phenyl}amino)pentyl]amino}phenyl)di-azen-1-yl]-1,3-thiazol-3-ium dichloride 3-methyl-2-[2-(4-{[5-({4-[2-(3-methyl-1,3-thiazol-3-ium-2-yl)diazen-1-yl]phenyl}amino)pentyl]amino}phenyl)di-azen-1-yl]-1,3-thiazol-3-ium dibromide 3-methyl-2-[2-(4-{[5-({4-[2-(3-methyl-1,3-thiazol-3-ium-2-yl)diazen-1-yl]phenyl}amino)pentyl]amino}phenyl)di-azen-1-yl]-1,3-thiazol-3-ium sulfate 3-methyl-2-[2-(4-{[5-({4-[2-(3-methyl-1,3-thiazol-3-ium-2-yl)diazen-1-yl]phenyl}amino)pentyl]amino}phenyl)di-azen-1-yl]-1,3-thiazol-3-ium di(toluenesulfonate)

3-methyl-2-[2-(4-{[5-({4-[2-(3-methyl-1,3-thiazol-3-ium-2-yl)diazen-1-yl]phenyl}amino)pentyl]amino}phenyl)di-azen-1-yl]-1,3-thiazol-3-ium di(methyl sulfate)

3-methyl-2-[2-(4-{[5-({4-[2-(3-methyl-1,3-thiazol-3-ium-2-yl)diazen-1-yl]phenyl}amino)pentyl]amino}phenyl)di-azen-1-yl]-1,3-thiazol-3-ium tetrachlorozincate 3-methyl-2-(2 4-{[methyl({3-[methyl({4-[2-(3-methyl-1,3-thiazol-3-ium-2-yl)diazen-1-yl]phenyl})amino]propyl})amino]phenyl}diazen-1-yl)-1,3-thiazol-3-ium dichloride 3-methyl-2-(2-{4-[methyl({3-[methyl({4-[2-(3-methyl-1,3-thiazol-3-ium-2-yl]phenyl})amino]propyl})amino]phenyl}diazen-1-yl)-1,3-thiazol-3-ium dibromide 3-methyl-2-(2-{4-[methyl({3-[methyl({4-[2-(3-methyl-1,3-thiazol-3-ium-2-yl]phenyl})amino]propyl})amino]phenyl}diazen-1-yl)-1,3-thiazol-3-ium sulfate 3-methyl-2-(2-{4-[methyl({3-[methyl({4-[2-(3-methyl-1,3-thiazol-3-ium-2-yl]phenyl})amino]propyl})amino]phenyl}diazen-1-yl)-1,3-thiazol-3-ium di(toluenesulfonate)

3-methyl-2-(2-{4-[methyl({3-[methyl({4-[2-(3-methyl-1,3-thiazol-3-ium-2-yl]phenyl})amino]propyl})amino]phenyl}diazen-1-yl)-1,3-thiazol-3-ium di(methyl sulfate)

3-methyl-2-(2-{4-[methyl({3-[methyl({4-[2-(3-methyl-1,3-thiazol-3-ium-2-yl]phenyl})amino]propyl})amino]phenyl}diazen-1-yl)-1,3-thiazol-3-ium tetrachlorozincate 3-methyl-2-(2-{4-[methyl({4-[methyl({4-[2-(3-methyl-1,3-thiazol-3-ium-2-yl)diazen-1-yl]phenyl})amino]butyl})amino]phenyl}diazen-1-yl)-1,3-thiazol-3-ium dichloride 3-methyl-2-(2-{4-[methyl({4-[methyl({4-[2-(3-methyl-1,3-thiazol-3-ium-2-yl)diazen-1-yl]phenyl})amino]butyl})amino]phenyl}diazen-1-yl)-1,3-thiazol-3-ium dibromide 3-methyl-2-(2-{4-[methyl({4-[methyl({4-[2-(3-methyl-1,3-thiazol-3-ium-2-yl)diazen-1-yl]phenyl})amino]butyl})amino]phenyl}diazen-1-yl)-1,3-thiazol-3-ium sulfate 3-methyl-2-(2-{4-[methyl({4-[methyl({4-[2-(3-methyl-1,3-thiazol-3-ium-2-yl)diazen-1-yl]phenyl})amino]butyl})amino]phenyl}diazen-1-yl)-1,3-thiazol-3-ium di(toluenesulfonate)

3-methyl-2-(2-{4-[methyl({4-[methyl({4-[2-(3-methyl-1,3-thiazol-3-ium-2-yl)diazen-1-yl]phenyl})amino]butyl})amino]phenyl}diazen-1-yl)-1,3-thiazol-3-ium di(methyl sulfate)

3-methyl-2-(2-{4-[methyl({4-[methyl({4-[2-(3-methyl-1,3-thiazol-3-ium-2-yl)diazen-1-yl]phenyl})amino]butyl})amino]phenyl}diazen-1-yl)-1,3-thiazol-3-ium tetrachlorozincate 3-methyl-2-(2 4-[methyl({5-[methyl({4-[2-(3-methyl-1,3-thiazol-3-ium-2-yl)diazen-1-yl]phenyl})amino]pentyl})amino]phenyl}diazen-1-yl)-1,3-thiazol-3-ium dichloride
3-methyl-2-(2 4-[methyl({5-[methyl({4-[2-(3-methyl-1,3-thiazol-3-ium-2-yl)diazen-1-yl]phenyl})amino]pentyl})amino]phenyl}diazen-1-yl)-1,3-thiazol-3-ium dibromide
3-methyl-2-(2-{4-[methyl({5-[methyl({4-[2-(3-methyl-1,3-thiazol-3-ium-2-yl)diazen-1-yl]phenyl})amino]pentyl})amino]phenyl}diazen-1-yl)-1,3-thiazol-3-ium sulfate
3-methyl-2-(2-{4-[methyl({5-[methyl({4-[2-(3-methyl-1,3-thiazol-3-ium-2-yl)diazen-1-yl]phenyl})amino]pentyl})amino]phenyl}diazen-1-yl)-1,3-thiazol-3-ium di(toluenesulfonate)
3-methyl-2-(2-{4-[methyl({5-[methyl({4-[2-(3-methyl-1,3-thiazol-3-ium-2-yl)diazen-1-yl]phenyl})amino]pentyl})amino]phenyl}diazen-1-yl)-1,3-thiazol-3-ium di(methyl sulfate)
3-methyl-2-(2-{4-[methyl({5-[methyl({4-[2-(3-methyl-1,3-thiazol-3-ium-2-yl)diazen-1-yl]phenyl})amino]pentyl})amino]phenyl}diazen-1-yl)-1,3-thiazol-3-ium tetrachlorozincate
2-(2-{4-[ethyl({3-[ethyl({4-[2-(3-methyl-1,3-thiazol-3-ium-2-yl)diazen-1-yl]phenyl})amino]propyl})amino]phenyl}diazen-1-yl)-3-methyl-1,3-thiazol-3-ium dichloride
2-(2-{4-[ethyl({3-[ethyl({4-[2-(3-methyl-1,3-thiazol-3-ium-2-yl)diazen-1-yl]phenyl})amino]propyl})amino]phenyl}diazen-1-yl)-3-methyl-1,3-thiazol-3-ium dibromide
2-(2-{4-[ethyl({3-[ethyl({4-[2-(3-methyl-1,3-thiazol-3-ium-2-yl)diazen-1-yl]phenyl})amino]propyl})amino]phenyl}diazen-1-yl)-3-methyl-1,3-thiazol-3-i sulfate
2-(2-{4-[ethyl({3-[ethyl({4-[2-(3-methyl-1,3-thiazol-3-ium-2-yl)diazen-1-yl]phenyl})amino]propyl})amino]phenyl}diazen-1-yl)-3-methyl-1,3-thiazol-3-ium di(toluenesulfonate)
2-(2-{4-[ethyl({3-[ethyl({4-[2-(3-methyl-1,3-thiazol-3-ium-2-yl)diazen-1-yl]phenyl})amino]propyl})amino]phenyl}diazen-1-yl)-3-methyl-1,3-thiazol-3-ium di(methyl sulfate)
2-(2-{4-[ethyl({3-[ethyl({4-[2-(3-methyl-1,3-thiazol-3-ium-2-yl)diazen-1-yl]phenyl})amino]propyl})amino]phenyl}diazen-1-yl)-3-methyl-1,3-thiazol-3-ium tetrachlorozincate
2-(2-{4-[ethyl({4-[ethyl({4-[2-(3-methyl-1,3-thiazol-3-ium-2-yl)diazen-1-yl]phenyl})amino]butyl})amino]phenyl}diazen-1-yl)-3-methyl-1,3-thiazol-3-ium dichloride
2-(2-{4-[ethyl({4-[ethyl({4-[2-(3-methyl-1,3-thiazol-3-ium-2-yl)diazen-1-yl]phenyl})amino]butyl})amino]phenyl}diazen-1-yl)-3-methyl-1,3-thiazol-3-ium dibromide
2-(2-{4-[ethyl({4-[ethyl({4-[2-(3-methyl-1,3-thiazol-3-ium-2-yl)diazen-1-yl]phenyl})amino]butyl})amino]phenyl}diazen-1-yl)-3-methyl-1,3-thiazol-3-ium sulfate
2-(2-{4-[ethyl({4-[ethyl({4-[2-(3-methyl-1,3-thiazol-3-ium-2-yl)diazen-1-yl]phenyl})amino]butyl})amino]phenyl}diazen-1-yl)-3-methyl-1,3-thiazol-3-ium di(toluenesulfonate)
2-(2-{4-[ethyl({4-[ethyl({4-[2-(3-methyl-1,3-thiazol-3-ium-2-yl)diazen-1-yl]phenyl})amino]butyl})amino]phenyl}diazen-1-yl)-3-methyl-1,3-thiazol-3-ium di(methyl sulfate)
2-(2-{4-[ethyl({4-[ethyl({4-[2-(3-methyl-1,3-thiazol-3-ium-2-yl)diazen-1-yl]phenyl})amino]butyl})amino]phenyl}diazen-1-yl)-3-methyl-1,3-thiazol-3-ium tetrachlorozincate
2-(2-{4-[ethyl({5-[ethyl({4-[2-(3-methyl-1,3-thiazol-3-ium-2-yl)diazen-1-yl]phenyl})amino]pentyl})amino]phenyl}diazen-1-yl)-3-methyl-1,3-thiazol-3-ium dichloride
2-(2-{4-[ethyl({5-[ethyl({4-[2-(3-methyl-1,3-thiazol-3-ium-2-yl)diazen-1-yl]phenyl})amino]pentyl})amino]phenyl}diazen-1-yl)-3-methyl-1,3-thiazol-3-ium dibromide
2-(2-{4-[ethyl({5-[ethyl({4-[2-(3-methyl-1,3-thiazol-3-ium-2-yl)diazen-1-yl]phenyl})amino]pentyl})amino]phenyl}diazen-1-yl)-3-methyl-1,3-thiazol-3-ium sulfate
2-(2-{4-[ethyl({5-[ethyl({4-[2-(3-methyl-1,3-thiazol-3-ium-2-yl)diazen-1-yl]phenyl})amino]pentyl})amino]phenyl}diazen-1-yl)-3-methyl-1,3-thiazol-3-ium di(toluenesulfonate)
2-(2-{4-[ethyl({5-[ethyl({4-[2-(3-methyl-1,3-thiazol-3-ium-2-yl)diazen-1-yl]phenyl})amino]pentyl})amino]phenyl}diazen-1-yl)-3-methyl-1,3-thiazol-3-ium di(methyl sulfate)
2-(2-{4-[ethyl({5-[ethyl({4-[2-(3-methyl-1,3-thiazol-3-ium-2-yl)diazen-1-yl]phenyl})amino]pentyl})amino]phenyl}diazen-1-yl)-3-methyl-1,3-thiazol-3-ium tetrachlorozincate
3-ethyl-2-[2-(4-{[3-({4-[2-(3-ethyl-1,3-thiazol-3-ium-2-yl)diazen-1-yl]phenyl}amino)propyl]amino}phenyl)diazen-1-yl]-1,3-thiazol-3-ium dichloride
3-ethyl-2-[2-(4-{[3-({4-[2-(3-ethyl-1,3-thiazol-3-ium-2-yl)diazen-1-yl]phenyl}amino)propyl]amino}phenyl)diazen-1-yl]-1,3-thiazol-3-ium dibromide
3-ethyl-2-[2-(4-{[3-({4-[2-(3-ethyl-1,3-thiazol-3-ium-2-yl)diazen-1-yl]phenyl}amino)propyl]amino}phenyl)diazen-1-yl]-1,3-thiazol-3-ium sulfate
3-ethyl-2-[2-(4-{[3-({4-[2-(3-ethyl-1,3-thiazol-3-ium-2-yl)diazen-1-yl]phenyl}amino)propyl]amino}phenyl)diazen-1-yl]-1,3-thiazol-3-ium di(toluenesulfonate)
3-ethyl-2-[2-(4-{[3-({4-[2-(3-ethyl-1,3-thiazol-3-ium-2-yl)diazen-1-yl]phenyl}amino)propyl]amino}phenyl)diazen-1-yl]-1,3-thiazol-3-ium di(methyl sulfate)
3-ethyl-2-[2-(4-{[3-({4-[2-(3-ethyl-1,3-thiazol-3-ium-2-yl)diazen-1-yl]phenyl}amino)propyl]amino}phenyl)diazen-1-yl]-1,3-thiazol-3-ium tetrachlorozincate
3-ethyl-2-[2-(4-{[4-({4-[2-(3-ethyl-1,3-thiazol-3-ium-2-yl)diazen-1-yl]phenyl}amino)butyl]amino}phenyl)diazen-1-yl]-1,3-thiazol-3-ium dichloride
3-ethyl-2-[2-(4-{[4-({4-[2-(3-ethyl-1,3-thiazol-3-ium-2-yl)diazen-1-yl]phenyl}amino)butyl]amino}phenyl)diazen-1-yl]-1,3-thiazol-3-ium dibromide
3-ethyl-2-[2-(4-{[4-({4-[2-(3-ethyl-1,3-thiazol-3-ium-2-yl)diazen-1-yl]phenyl}amino)butyl]amino}phenyl)diazen-1-yl]-1,3-thiazol-3-ium sulfate
3-ethyl-2-[2-(4-{[4-({4-[2-(3-ethyl-1,3-thiazol-3-ium-2-yl)diazen-1-yl]phenyl}amino)butyl]amino}phenyl)diazen-1-yl]-1,3-thiazol-3-ium di(toluenesulfonate)
3-ethyl-2-[2-(4-{[4-({4-[2-(3-ethyl-1,3-thiazol-3-ium-2-yl)diazen-1-yl]phenyl}amino)butyl]amino}phenyl)diazen-1-yl]-1,3-thiazol-3-ium di(methyl sulfate)
3-ethyl-2-[2-(4-{[4-({4-[2-(3-ethyl-1,3-thiazol-3-ium-2-yl)diazen-1-yl]phenyl}amino)butyl]amino}phenyl)diazen-1-yl]-1,3-thiazol-3-ium tetrachlorozincate
3-ethyl-2-[2-(4-{[5-({4-[2-(3-ethyl-1,3-thiazol-3-ium-2-yl)diazen-1-yl]phenyl}amino)pentyl]amino}phenyl)diazen-1-yl]-1,3-thiazol-3-ium dichloride
3-ethyl-2-[2-(4-{[5-({4-[2-(3-ethyl-1,3-thiazol-3-ium-2-yl)diazen-1-yl]phenyl}amino)pentyl]amino}phenyl)diazen-1-yl]-1,3-thiazol-3-ium dibromide 3-ethyl-2-[2-(4-{[5-({4-[2-(3-ethyl-1,3-thiazol-3-ium-2-yl)
diazen-1-yl]phenyl}amino)pentyl]amino}phenyl)diazen-
1-yl]-1,3-thiazol-3-ium sulfate
3-ethyl-2-[2-(4-{[5-({4-[2-(3-ethyl-1,3-thiazol-3-ium-2-yl)
diazen-1-yl]phenyl}amino)pentyl]amino}phenyl)diazen-
1-yl]-1,3-thiazol-3-ium di(toluenesulfonate)
3-ethyl-2-[2-(4-{[5-({4-[2-(3-ethyl-1,3-thiazol-3-ium-2-yl)
diazen-1-yl]phenyl}amino)pentyl]amino}phenyl)diazen-
1-yl]-1,3-thiazol-3-ium di(methyl sulfate)
3-ethyl-2-[2-(4-{[5-({4-[2-(3-ethyl-1,3-thiazol-3-ium-2-yl)
diazen-1-yl]phenyl}amino)pentyl]amino}phenyl)diazen-
1-yl]-1,3-thiazol-3-ium tetrachlorozincate
3-ethyl-2-[2-(4-{[3-({4-[2-(3-ethyl-1,3-thiazol-3-ium-2-yl)
diazen-1-yl]phenyl}(methyl)amino)propyl](methyl)
amino}phenyl)diazen-1-yl]-1,3-thiazol-3-ium dichloride
3-ethyl-2-[2-(4-{[3-({4-[2-(3-ethyl-1,3-thiazol-3-ium-2-yl)
diazen-1-yl]phenyl}(methyl)amino)propyl](methyl)
amino}phenyl)diazen-1-yl]-1,3-thiazol-3-ium dibromide
3-ethyl-2-[2-(4-{[3-({4-[2-(3-ethyl-1,3-thiazol-3-ium-2-yl)
diazen-1-yl]phenyl}(methyl)amino)propyl](methyl)
amino}phenyl)diazen-1-yl]-1,3-thiazol-3-ium sulfate
3-ethyl-2-[2-(4-{[3-({4-[2-(3-ethyl-1,3-thiazol-3-ium-2-yl)
diazen-1-yl]phenyl}(methyl)amino)propyl](methyl)
amino}phenyl)diazen-1-yl]-1,3-thiazol-3-ium di (toluenesulfonate)
3-ethyl-2-[2-(4-{[3-({4-[2-(3-ethyl-1,3-thiazol-3-ium-2-yl)
diazen-1-yl]phenyl}(methyl)amino)propyl](methyl)
amino}phenyl)diazen-1-yl]-1,3-thiazol-3-ium di(methyl sulfate)
3-ethyl-2-[2-(4-{[3-({4-[2-(3-ethyl-1,3-thiazol-3-ium-2-yl)
diazen-1-yl]phenyl}(methyl)amino)propyl](methyl)
amino}phenyl)diazen-1-yl]-1,3-thiazol-3-ium tetrachlorozincate
3-ethyl-2-[2-(4-{[4-({4-[2-(3-ethyl-1,3-thiazol-3-ium-2-yl)
diazen-1-yl]phenyl}(methyl)amino)butyl](methyl)
amino}phenyl)diazen-1-yl]-1,3-thiazol-3-ium dichloride
3-ethyl-2-[2-(4-{[4-({4-[2-(3-ethyl-1,3-thiazol-3-ium-2-yl)diazen-1-yl]phenyl}(methyl)amino)butyl](methyl)
amino}phenyl)diazen-1-yl]-1,3-thiazol-3-ium dibromide
3-ethyl-2-[2-(4-{[4-({4-[2-(3-ethyl-1,3-thiazol-3-ium-2-yl)
diazen-1-1]phenyl}(methyl)amino)butyl](methyl)
amino}phenyl)diazen-1-yl]-1,3-thiazol-3-ium sulfate
3-ethyl-2-[2-(4-{[4-({4-[2-(3-ethyl-1,3-thiazol-3-ium-2-yl)
diazen-1-yl]phenyl}(methyl)amino)butyl](methyl)
amino}phenyl)diazen-1-yl]-1,3-thiazol-3-ium di(toluenesulfonate)
3-ethyl-2-[2-(4-{[4-({4-[2-(3-ethyl-1,3-thiazol-3-ium-2-yl)
diazen-1-yl]phenyl}(methyl)amino)butyl](methyl)
amino}phenyl)diazen-1-yl]-1,3-thiazol-3-ium di(methyl sulfate)
3-ethyl-2-[2-(4-{[4-({4-[2-(3-ethyl-1,3-thiazol-3-ium-2-yl)
diazen-1-yl]phenyl}(methyl)amino)butyl](methyl)
amino}phenyl)diazen-1-yl]-1,3-thiazol-3-ium
3-ethyl-2-[2-(4-{[5-({4-[2-(3-ethyl-1,3-thiazol-3-ium-2-yl)
diazen-1-yl]phenyl}(methyl)amino)pentyl](methyl)
amino}phenyl)diazen-1-yl]-1,3-thiazol-3-ium dichloride
3-ethyl-2-[2-(4-{[5-({4-[2-(3-ethyl-1,3-thiazol-3-ium-2-yl)
diazen-1-yl]phenyl}(methyl)amino)pentyl](methyl)
amino}phenyl)diazen-1-yl]-1,3-thiazol-3-ium dibromide
3-ethyl-2-[2-(4-{[5-({4-[2-(3-ethyl-1,3-thiazol-3-ium-2-yl)
diazen-1-yl]phenyl}(methyl)amino)pentyl](methyl)
amino}phenyl)diazen-1-yl]-1,3-thiazol-3-ium sulfate
3-ethyl-2-[2-(4-{[5-({4-[2-(3-ethyl-1,3-thiazol-3-ium-2-yl)
diazen-1-yl]phenyl}(methyl)amino)pentyl](methyl)
amino}phenyl)diazen-1-yl]-1,3-thiazol-3-ium di(toluenesulfonate)

3-ethyl-2-[2-(4-{[5-({4-[2-(3-ethyl-1,3-thiazol-3-ium-2-yl)
diazen-1-yl]phenyl}(methyl)amino)pentyl](methyl)
amino}phenyl)diazen-1-yl]-1,3-thiazol-3-ium di(methyl sulfate)
3-ethyl-2-[2-(4-{[5-({4-[2-(3-ethyl-1,3-thiazol-3-ium-2-yl)
diazen-1-yl]phenyl}(methyl)amino)pentyl](methyl)
amino}phenyl)diazen-1-yl]-1,3-thiazol-3-ium tetrachlorozincate
3-ethyl-2-(2-{4-[ethyl({3-[ethyl({4-[2-(3-ethyl-1,3-thiazol-3-ium-2-yl)diazen-1-yl]phenyl})amino]propyl})amino]
phenyl}diazen-1-yl)-1,3-thiazol-3-ium dichloride
3-ethyl-2-(2-{4-[ethyl({3-[ethyl({4-[2-(3-ethyl-1,3-thiazol-3-ium-2-yl)diazen-1-yl]phenyl}amino]propyl})amino]
phenyl}diazen-1-yl)-1,3-thiazol-3-ium dibromide
3-ethyl-2-(2-{4-[ethyl({3-[ethyl({4-[2-(3-ethyl-1,3-thiazol-3-ium-2-yl)diazen-1-yl]phenyl}amino]propyl})amino]
phenyl}diazen-1-yl)-1,3-thiazol-3-ium sulfate
3-ethyl-2-(2-{4-[ethyl({3-[ethyl({4-[2-(3-ethyl-1,3-thiazol-3-ium-2-yl)diazen-1-yl]phenyl}amino]propyl})amino]
phenyl}diazen-1-yl)-1,3-thiazol-3-ium di(toluenesulfonate)
3-ethyl-2-(2-{4-[ethyl({3-[ethyl({4-[2-(3-ethyl-1,3-thiazol-3-ium-2-yl)diazen-1-yl]phenyl}amino]propyl})amino]
phenyl}diazen-1-yl)-1,3-thiazol-3-ium di(methyl sulfate)
3-ethyl-2-(2-{4-[ethyl({3-[ethyl({4-[2-(3-ethyl-1,3-thiazol-3-ium-2-yl)diazen-1-yl]phenyl}amino]propyl})amino]
phenyl}diazen-1-yl)-1,3-thiazol-3-ium tetrachlorozincate
3-ethyl-2-(2-{4-[ethyl({4-[ethyl({4-[2-(3-ethyl-1,3-thiazol-3-ium-2-yl)diazen-1-yl]phenyl}amino]butyl})amino]
phenyl}diazen-1-yl)-1,3-thiazol-3-ium dichloride
3-ethyl-2-(2-{4-[ethyl({4-[ethyl({4-[2-(3-ethyl-1,3-thiazol-3-ium-2-yl)diazen-1-yl]phenyl}amino]butyl})amino]
phenyl}diazen-1-yl)-1,3-thiazol-3-ium dibromide
3-ethyl-2-(2-{4-[ethyl({4-[ethyl({4-[2-(3-ethyl-1,3-thiazol-3-ium-2-yl)diazen-1-yl]phenyl}amino]butyl})amino]
phenyl}diazen-1-yl)-1,3-thiazol-3-ium sulfate
3-ethyl-2-(2-{4-[ethyl({4-[ethyl({4-[2-(3-ethyl-1,3-thiazol-3-ium-2-yl)diazen-1-yl]phenyl}amino]butyl})amino]
phenyl}diazen-1-yl)-1,3-thiazol-3-ium di(toluenesulfonate)
3-ethyl-2-(2-{4-[ethyl({4-[ethyl({4-[2-(3-ethyl-1,3-thiazol-3-ium-2-yl)diazen-1-yl]phenyl}amino]butyl})amino]
phenyl}diazen-1-yl)-1,3-thiazol-3-ium di(methyl sulfate)
3-ethyl-2-(2-{4-[ethyl({4-[ethyl({4-[2-(3-ethyl-1,3-thiazol-3-ium-2-yl)diazen-1-yl]phenyl}amino]butyl})amino]
phenyl}diazen-1-yl)-1,3-thiazol-3-ium tetrachlorozincate
3-ethyl-2-(2-{4-[ethyl({5-[ethyl({4-[2-(3-ethyl-1,3-thiazol-3-ium-2-yl)diazen-1-yl]phenyl}amino]pentyl}amino]
phenyl}diazen-1-yl)-1,3-thiazol-3-ium dichloride
3-ethyl-2-(2-{4-[ethyl({5-[ethyl({4-[2-(3-ethyl-1,3-thiazol-3-ium-2-yl)diazen-1-yl]phenyl}amino]pentyl}amino]
phenyl}diazen-1-yl)-1,3-thiazol-3-ium dibromide
3-ethyl-2-(2-{4-[ethyl({5-[ethyl({4-[2-(3-ethyl-1,3-thiazol-3-ium-2-yl)diazen-1-yl]phenyl}amino]pentyl}amino]
phenyl}diazen-1-yl)-1,3-thiazol-3-ium sulfate
3-ethyl-2-(2-{4-[ethyl({5-[ethyl({4-[2-(3-ethyl-1,3-thiazol-3-ium-2-yl)diazen-1-yl]phenyl}amino]pentyl}amino]
phenyl}diazen-1-yl)-1,3-thiazol-3-ium di(toluenesulfonate)
3-ethyl-2-(2-{4-[ethyl({5-[ethyl({4-[2-(3-ethyl-1,3-thiazol-3-ium-2-yl)diazen-1-yl]phenyl}amino]pentyl}amino]
phenyl}diazen-1-yl)-1,3-thiazol-3-ium di(methyl sulfate)
3-ethyl-2-(2-{4-[ethyl({5-[ethyl({4-[2-(3-ethyl-1,3-thiazol-3-ium-2-yl)diazen-1-yl]phenyl}amino]pentyl}amino]
phenyl}diazen-1-yl)-1,3-thiazol-3-ium tetrachlorozincate 3-methyl-2-{2-[4-({2-[2-({4-[2-(3-methyl-1,3-thiazol-3-ium-2-yl)diazen-1-yl]phenyl}amino)ethoxy]ethyl}amino)phenyl]diazen-1-yl}-1,3-thiazol-3-ium dichloride 3-methyl-2-{2-[4-({2-[2-({4-[2-(3-methyl-1,3-thiazol-3-ium-2-yl)diazen-1-yl]phenyl}amino)ethoxy]ethyl}amino)phenyl]diazen-1-yl}-1,3-thiazol-3-ium dibromide 3-methyl-2-{2-[4-({2-[2-({4-[2-(3-methyl-1,3-thiazol-3-ium-2-yl)diazen-1-yl]phenyl}amino)ethoxy]ethyl}amino)phenyl]diazen-1-yl}-1,3-thiazol-3-ium sulfate 3-methyl-2-{2-[4-({2-[2-({4-[2-(3-methyl-1,3-thiazol-3-ium-2-yl)diazen-1-yl]phenyl}amino)ethoxy]ethyl}amino)phenyl]diazen-1-yl}-1,3-thiazol-3-ium di(toluenesulfonate)

3-methyl-2-{2-[4-({2-[2-({4-[2-(3-methyl-1,3-thiazol-3-ium-2-yl)diazen-1-yl]phenyl}amino)ethoxy]ethyl}amino)phenyl]diazen-1-yl}-1,3-thiazol-3-ium di(methyl sulfate)

3-methyl-2-{2-[4-({2-[2-({4-[2-(3-methyl-1,3-thiazol-3-ium-2-yl)diazen-1-yl]phenyl}amino)ethoxy]ethyl}amino)phenyl]diazen-1-yl}-1,3-thiazol-3-ium tetrachlorozincate 3-methyl-2-(2-{4-[methyl(2-{2-[methyl({4-[2-(3-methyl-1,3-thiazol-3-ium-2-yl)diazen-1-yl]phenyl})amino]ethoxy}ethyl)amino]phenyl}diazen-1-yl)-1,3-thiazol-3-ium dichloride 3-methyl-2-(2-{4-[methyl(2-{2-[methyl({4-[2-(3-methyl-1,3-thiazol-3-ium-2-yl)diazen-1-yl]phenyl})amino]ethoxy}ethyl)amino]phenyl}diazen-1-yl)-1,3-thiazol-3-ium dibromide 3-methyl-2-(2-{4-[methyl(2-{2-[methyl({4-[2-(3-methyl-1,3-thiazol-3-ium-2-yl)diazen-1-yl]phenyl})amino]ethoxy}ethyl)amino]phenyl}diazen-1-yl)-1,3-thiazol-3-ium sulfate 3-methyl-2-(2-{4-[methyl(2-{2-[methyl({4-[2-(3-methyl-1,3-thiazol-3-ium-2-yl)diazen-1-yl]phenyl})amino]ethoxy}ethyl)amino]phenyl}diazen-1-yl)-1,3-thiazol-3-ium di(toluenesulfonate)

3-methyl-2-(2-{4-[methyl(2-{2-[methyl({4-[2-(3-methyl-1,3-thiazol-3-ium-2-yl)diazen-1-yl]phenyl})amino]ethoxy}ethyl)amino]phenyl}diazen-1-yl)-1,3-thiazol-3-ium di(methyl sulfate)

3-methyl-2-(2-{4-[methyl(2-{2-[methyl({4-[2-(3-methyl-1,3-thiazol-3-ium-2-yl)diazen-1-yl]phenyl})amino]ethoxy}ethyl)amino]phenyl}diazen-1-yl)-1,3-thiazol-3-ium tetrachlorozincate 2-(2-{4-[ethyl(2-{2-[ethyl({4-[2-(3-methyl-1,3-thiazol-3-ium-2-yl)diazen-1-yl]phenyl})amino]ethoxy}ethyl)amino]phenyl}diazen-1-yl)-3-methyl-1,3-thiazol-3-ium dichloride 2-(2-{4-[ethyl(2-{2-[ethyl({4-[2-(3-methyl-1,3-thiazol-3-ium-2-yl)diazen-1-yl]phenyl})amino]ethoxy}ethyl)amino]phenyl}diazen-1-yl)-3-methyl-1,3-thiazol-3-ium dibromide 2-(2-{4-[ethyl(2-{2-[ethyl({4-[2-(3-methyl-1,3-thiazol-3-ium-2-yl)diazen-1-yl]phenyl})amino]ethoxy}ethyl)amino]phenyl}diazen-1-yl)-3-methyl-1,3-thiazol-3-ium sulfate 2-(2-{4-[ethyl(2-{2-[ethyl({4-[2-(3-methyl-1,3-thiazol-3-ium-2-yl)diazen-1-yl]phenyl})amino]ethoxy}-ethyl)amino]phenyl}diazen-1-yl)-3-methyl-1,3-thiazol-3-ium di(toluenesulfonate)

2-(2-{4-[ethyl(2-{2-[ethyl({4-[2-(3-methyl-1,3-thiazol-3-ium-2-yl)diazen-1-yl]phenyl})amino]-ethoxy}ethyl)amino]phenyl}diazen-1-yl)-3-methyl-1,3-thiazol-3-ium di(methyl sulfate)

2-(2-{4-[ethyl(2-{2-[ethyl({4-[2-(3-methyl-1,3-thiazol-3-ium-2-yl)diazen-1-yl]phenyl})amino]-ethoxy}ethyl)amino]phenyl}diazen-1-yl)-3-methyl-1,3-thiazol-3-ium tetrachlorozincate 3-ethyl-2-{2-[4-({2-[2-({4-[2-(3-ethyl-1,3-thiazol-3-ium-2-yl)diazen-1-yl]phenyl}amino)ethoxy]ethyl}amino)phenyl]diazen-1-yl}-1,3-thiazol-3-ium dichloride 3-ethyl-2-{2-[4-({2-[2-({4-[2-(3-ethyl-1,3-thiazol-3-ium-2-yl)diazen-1-yl]phenyl}amino)ethoxy]ethyl}amino)phenyl]diazen-1-yl}-1,3-thiazol-3-ium dibromide 3-ethyl-2-{2-[4-({2-[2-({4-[2-(3-ethyl-1,3-thiazol-3-ium-2-yl)diazen-1-yl]phenyl}amino)ethoxy]ethyl}amino)phenyl]diazen-1-yl}-1,3-thiazol-3-ium sulfate 3-ethyl-2-{2-[4-({2-[2-({4-[2-(3-ethyl-1,3-thiazol-3-ium-2-yl)diazen-1-yl]phenyl}amino)ethoxy]ethyl}amino)phenyl]diazen-1-yl}-1,3-thiazol-3-ium di(toluenesulfonate)

3-ethyl-2-{2-[4-({2-[2-({4-[2-(3-ethyl-1,3-thiazol-3-ium-2-yl)diazen-1-yl]phenyl}amino)ethoxy]ethyl}amino)phenyl]diazen-1-yl}-1,3-thiazol-3-ium di(methyl sulfate)

3-ethyl-2-{2-[4-({2-[2-({4-[2-(3-ethyl-1,3-thiazol-3-ium-2-yl)diazen-1-yl]phenyl}amino)ethoxy]ethyl}amino)phenyl]diazen-1-yl}-1,3-thiazol-3-ium tetrachlorozincate 3-ethyl-2-{2-[4-({2-[2-({4-[2-(3-ethyl-1,3-thiazol-3-ium-2-yl)diazen-1-yl]phenyl}(methyl)amino)ethoxy]-ethyl}(methyl)amino)phenyl]diazen-1-yl}-1,3-thiazol-3-ium dichloride 3-ethyl-2-{2-[4-({2-[2-({4-[2-(3-ethyl-1,3-thiazol-3-ium-2-yl)diazen-1-yl]phenyl}(methyl)amino)-ethoxy]ethyl}(methyl)amino)phenyl]diazen-1-yl}-1,3-thiazol-3-ium dibromide 3-ethyl-2-{2-[4-({2-[2-({4-[2-(3-ethyl-1,3-thiazol-3-ium-2-yl)diazen-1-yl]phenyl}(methyl)amino)-ethoxy]ethyl}(methyl)amino)phenyl]diazen-1-yl}-1,3-thiazol-3-ium sulfate 3-ethyl-2-{2-[4-({2-[2-({4-[2-(3-ethyl-1,3-thiazol-3-ium-2-yl)diazen-1-yl]phenyl}(methyl)amino)-ethoxy]ethyl}(methyl)amino)phenyl]diazen-1-yl}-1,3-thiazol-3-ium di(toluenesulfonate)

3-ethyl-2-{2-[4-({2-[2-({4-[2-(3-ethyl-1,3-thiazol-3-ium-2-yl)diazen-1-yl]phenyl}(methyl)amino)-ethoxy]ethyl}(methyl)amino)phenyl]diazen-1-yl}-1,3-thiazol-3-ium di(methyl sulfate)

3-ethyl-2-{2-[4-({2-[2-({4-[2-(3-ethyl-1,3-thiazol-3-ium-2-yl)diazen-1-yl]phenyl}(methyl)amino)-ethoxy]ethyl}(methyl)amino)phenyl]diazen-1-yl}-1,3-thiazol-3-ium tetrachlorozincate 3-ethyl-2-(2-{4-[ethyl(2-{2-[ethyl({4-[2-(3-ethyl-1,3-thiazol-3-ium-2-yl)diazen-1-yl]phenyl}amino]-ethoxy}ethyl)amino]phenyl}diazen-1-yl)-1,3-thiazol-3-ium dichloride 3-ethyl-2-(2-{4-[ethyl(2-{2-[ethyl({4-[2-(3-ethyl-1,3-thiazol-3-ium-2-yl)diazen-1-yl]phenyl}amino]-ethoxy}ethyl)amino]phenyl}diazen-1-yl)-1,3-thiazol-3-ium dibromide 3-ethyl-2-(2-{4-[ethyl(2-{2-[ethyl({4-[2-(3-ethyl-1,3-thiazol-3-ium-2-yl)diazen-1-yl]phenyl}amino]-ethoxy}ethyl)amino]phenyl}diazen-1-yl)-1,3-thiazol-3-ium sulfate 3-ethyl-2-(2-{4-[ethyl(2-{2-[ethyl({4-[2-(3-ethyl-1,3-thiazol-3-ium-2-yl)diazen-1-yl]phenyl}amino]-ethoxy}ethyl)amino]phenyl}diazen-1-yl)-1,3-thiazol-3-ium di(toluenesulfonate)

3-ethyl-2-(2-{4-[ethyl(2-{2-[ethyl({4-[2-(3-ethyl-1,3-thiazol-3-ium-2-yl)diazen-1-yl]phenyl}amino]-ethoxy}ethyl)amino]phenyl}diazen-1-yl)-1,3-thiazol-3-ium di(methyl sulfate)

3-ethyl-2-(2-{4-[ethyl(2-{2-[ethyl({4-[2-(3-ethyl-1,3-thiazol-3-ium-2-yl)diazen-1-yl]phenyl}amino]-ethoxy}ethyl)amino]phenyl}diazen-1-yl)-1,3-thiazol-3-ium tetrachlorozincate 3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium dichloride 3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium dibromide 3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium sulfate 3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium di(toluenesulfonate)

3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium di(methyl sulfate)

3-methyl-2-{2-[4-(10-{4-[2-(3-methyl-1,3-thiazol-3-ium-2-yl)diazen-1-yl]phenyl}-4,7-dioxa-1,10-diazadecan-1-yl)phenyl]diazen-1-yl}-1,3-thiazol-3-ium tetrachlorozincate 3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium dichloride 3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium dibromide 3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium sulfate 3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium di(toluenesulfonate)

3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium di(methyl sulfate)

3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium tetrachlorozincate 3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium dichloride 3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium dibromide 3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium sulfate 3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium di(toluenesulfonate)

3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium di(methyl sulfate)

3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium tetrachlorozincate 3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium dichloride 3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium dibromide 3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium sulfate 3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium di(toluenesulfonate)

3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium di(methyl sulfate)

3-ethyl-2-{2-[4-(10-{4-[2-(3-ethyl-1,3-thiazol-3-ium-2-yl)diazen-1-yl]phenyl}-4,7-dioxa-1,10-diazadecan-1-yl)phenyl]diazen-1-yl}-1,3-thiazol-3-ium tetrachlorozincate 3-ethyl-2-{2-[4-(11-{4-[2-(3-ethyl-1,3-thiazol-3-ium-2-yl)diazen-1-yl]phenyl}-5,8-dioxa-2 1 1-diazadodecan-2-yl)phenyl]diazen-1-yl}-1,3-thiazol-3-ium dichloride 3-ethyl-2-{2-[4-(11-{4-[2-(3-ethyl-1,3-thiazol-3-ium-2-yl)diazen-1-yl]phenyl}-5,8-dioxa-2 1 1-diazadodecan-2-yl)phenyl]diazen-1-yl}-1,3-thiazol-3-ium dibromide 3-ethyl-2-{2-[4-(11-{4-[2-(3-ethyl-1,3-thiazol-3-ium-2-yl)diazen-1-yl]phenyl}-5,8-dioxa-2 1 1-diazadodecan-2-yl)phenyl]diazen-1-yl}-1,3-thiazol-3-ium sulfate 3-ethyl-2-{2-[4-(11-{4-[2-(3-ethyl-1,3-thiazol-3-ium-2-yl)diazen-1-yl]phenyl}-5,8-dioxa-2 1 1-diazadodecan-2-yl)phenyl]diazen-1-yl}-1,3-thiazol-3-ium di(toluenesulfonate)

3-ethyl-2-{2-[4-(11-{4-[2-(3-ethyl-1,3-thiazol-3-ium-2-yl)diazen-1-yl]phenyl}-5,8-dioxa-2 1 1-diazadodecan-2-yl)phenyl]diazen-1-yl}-1,3-thiazol-3-ium di(methyl sulfate)

3-ethyl-2-{2-[4-(11-{4-[2-(3-ethyl-1,3-thiazol-3-ium-2-yl)diazen-1-yl]phenyl}-5,8-dioxa-2 1 1-diazadodecan-2-yl)phenyl]diazen-1-yl}-1,3-thiazol-3-ium tetrachlorozincate 3-ethyl-2-{2-[4-(12-{4-[2-(3-ethyl-1,3-thiazol-3-ium-2-yl)diazen-1-yl]phenyl}-6,9-dioxa-3 12-diazatetradecan-3-yl)phenyl]diazen-1-yl}-1,3-thiazol-3-ium dichloride 3-ethyl-2-{2-[4-(12-{4-[2-(3-ethyl-1,3-thiazol-3-ium-2-yl)diazen-1-yl]phenyl}-6,9-dioxa-3 12-diazatetradecan-3-yl)phenyl]diazen-1-yl}-1,3-thiazol-3-ium dibromide 3-ethyl-2-{2-[4-(12-{4-[2-(3-ethyl-1,3-thiazol-3-ium-2-yl)diazen-1-yl]phenyl}-6,9-dioxa-3 12-diazatetradecan-3-yl)phenyl]diazen-1-yl}-1,3-thiazol-3-ium sulfate 3-ethyl-2-{2-[4-(12-{4-[2-(3-ethyl-1,3-thiazol-3-ium-2-yl)diazen-1-yl]phenyl}-6,9-dioxa-3 12-diazatetradecan-3-yl)phenyl]diazen-1-yl}-1,3-thiazol-3-ium di(toluenesulfonate)

3-ethyl-2-{2-[4-(12-{4-[2-(3-ethyl-1,3-thiazol-3-ium-2-yl)diazen-1-yl]phenyl}-6,9-dioxa-3 12-diazatetradecan-3-yl)phenyl]diazen-1-yl}-1,3-thiazol-3-ium di(methyl sulfate) and/or 3-ethyl-2-{2-[4-(12-{4-[2-(3-ethyl-1,3-thiazol-3-ium-2-yl)diazen-1-yl]phenyl}-6,9-dioxa-3 12-diazatetradecan-3-yl)phenyl]diazen-1-yl}-1,3-thiazol-3-ium tetrachlorozincate.

Within the scope of the works carried out for various embodiments of the present disclosure, it has been found that particularly intense colorings in the blue range could be attained with the direct dyes (a) of formula (I) if R1, R4 independently of one another stand for a methyl group or an ethyl group,
R2, R3 independently of one another stand for a hydrogen atom, for a methyl group, or for an ethyl group,
R5, R6, R7, R8 each stand for a hydrogen atom,
Q stands for a grouping of formula (II),

*—(CH$_2$)$_n$-*          (II)

and
n stands for the number 3 or 4.

Explicitly very particularly preferred agents according to an exemplary embodiment of the present disclosure for dyeing keratin fibers are therefore those which contain at least one dye (a) of formula (I) which is selected from the group of Salts of 3-methyl-2-[2-(4-{[3-({4-[2-(3-methyl-1,3-thiazol-3-ium-2-yl)diazen-1-yl]phenyl}amino)propyl]amino}phenyl)diazen-1-yl]-1,3-thiazol-3-ium

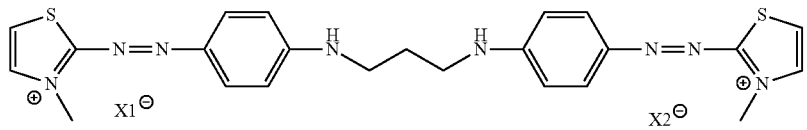

Salts of 3-methyl-2-[2-(4-{[4-({4-[2-(3-methyl-1,3-thiazol-3-ium-2-yl)diazen-1-yl]phenyl}amino)butyl]amino}phenyl)diazen-1-yl]-1,3-thiazol-3-ium

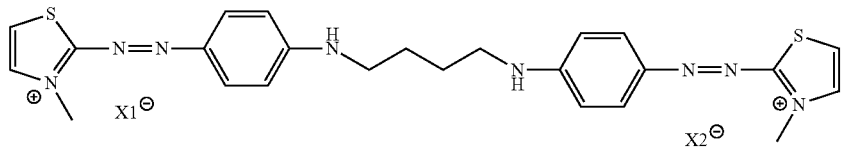

Salts of 3-methyl-2-(2-{4-[methyl({3-[methyl({4-[2-(3-methyl-1,3-thiazol-3-ium-2-yl)diazen-1-yl]phenyl})amino]propyl})amino]phenyl}diazen-1-yl)-1,3-thiazol-3-ium

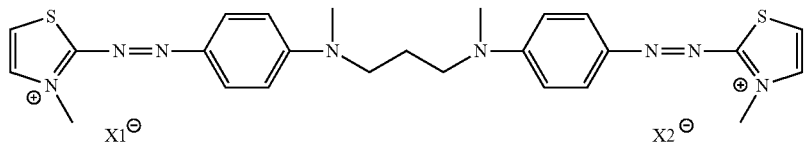

Salts of 3-methyl-2-(2-{4-[methyl({4-[methyl({4-[2-(3-methyl-1,3-thiazol-3-ium-2-yl)diazen-1-yl]phenyl})amino]butyl})amino]phenyl}diazen-1-yl)-1,3-thiazol-3-ium

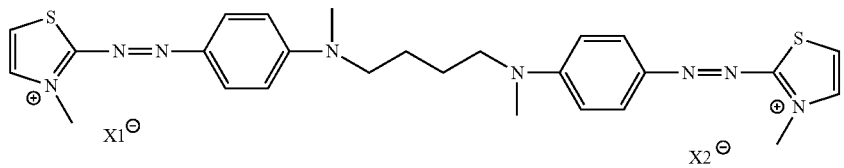

Salts of 2-(2-{4-[ethyl({3-[ethyl({4-[2-(3-methyl-1,3-thiazol-3-ium-2-yl)diazen-1-yl]phenyl})amino]propyl})amino]phenyl}diazen-1-yl)-3-methyl-1,3-thiazol-3-ium

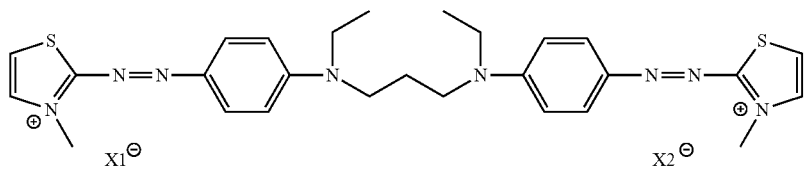

Salts of 2-(2-{4-[ethyl({4-[ethyl({4-[2-(3-methyl-1,3-thiazol-3-ium-2-yl)diazen-1-yl]phenyl})amino]butyl})amino]phenyl}diazen-1-yl)-3-methyl-1,3-thiazol-3-ium

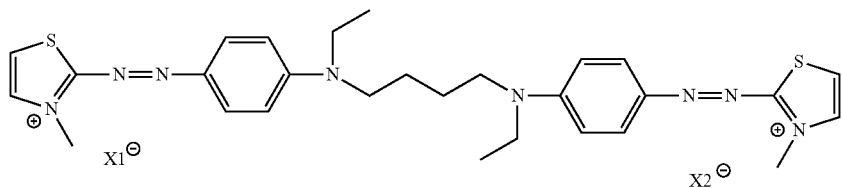

Salts of 3-ethyl-2-[2-(4-{[3-({4-[2-(3-ethyl-1,3-thiazol-3-ium-2-yl)diazen-1-yl]phenyl}amino)propyl]amino}phenyl)diazen-1-yl]-1,3-thiazol-3

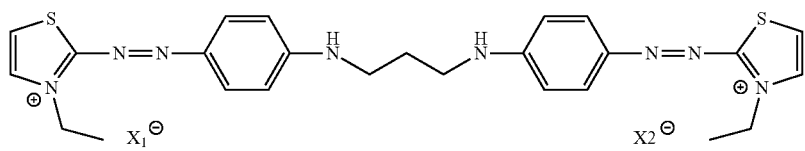

Salts of 3-ethyl-2-[2-(4-{[4-({4-[2-(3-ethyl-1,3-thiazol-3-ium-2-yl)diazen-1-yl]phenyl}amino)butyl]amino}phenyl)diazen-1-yl]-1,3-thiazol-3-ium

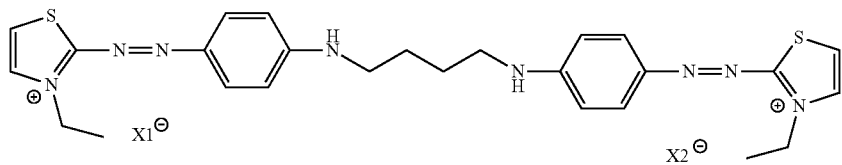

Salts of 3-ethyl-2-[2-(4-{[3-({4-[2-(3-ethyl-1,3-thiazol-3-ium-2-yl)diazen-1-yl]phenyl}(methyl)amino)propyl](methyl)amino}phenyl)diazen-1-yl]-1,3-thiazol-3-

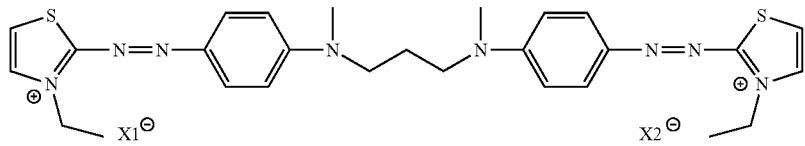

Salts of 3-ethyl-2-[2-(4-{[4-({4-[2-(3-ethyl-1,3-thiazol-3-ium-2-yl)diazen-1-yl]phenyl}(methyl)amino)butyl](methyl)amino}phenyl)diazen-1-yl]-1,3-thiazol-3-

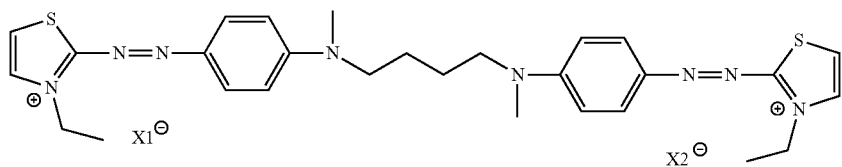

Salts of 3-ethyl-2-(2-{4-[ethyl({3-[ethyl({4-[2-(3-ethyl-1,3-thiazol-3-ium-2-yl)diazen-1-1]phenyl})amino]propyl})amino]phenyl}diazen-1-yl)-1,3-thiazol-3-ium

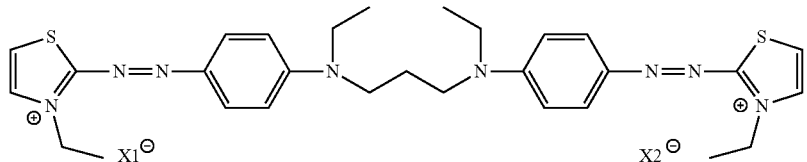

Salts of 3-ethyl-2-(2-{4-[ethyl({4-[ethyl({4-[2-(3-ethyl-1,3-thiazol-3-ium-2-yl)diazen-1-yl]phenyl})amino]butyl})amino]phenyl}diazen-1-yl)-1,3-thiazol-3-ium

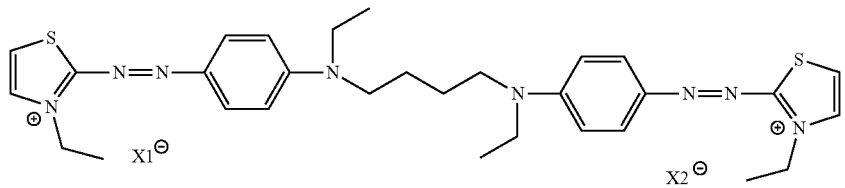

The agents according to an exemplary embodiment of the present disclosure for dyeing keratin fibers contain the direct dye(s) of formula (I) preferably in a total amount of from about 0.01 to about 4.5% by weight, preferably from about 0.05 to about 2.8% by weight, more preferably from about 0.1 to about 2.2% by weight, and particularly preferably from about 0.2 to about 1.2% by weight. The specified amount in % by weight relates here to the total amount of all compounds of formula (I) contained in the agent and is set in relation to the total weight of the agent.

In a further preferred embodiment an agent according to the present disclosure for dyeing keratin fibers is therefore characterized in that it contains in relation to the total weight of the agent one or more direct dyes (a) of formula (I) in a total amount of from about 0.01 to about 4.5% by weight, preferably from about 0.05 to about 2.8% by weight, more preferably from about 0.1 to about 2.2% by weight, and particularly preferably from about 0.2 to about 1.2% by weight.

The dyes of general formula (I) can be produced for example by a method as is described in WO 2002/100369 A2.

By way of example, the reactant 2-aminothiazole can be reacted in concentrated sulfuric acid with nitrosylsulfuric acid to form the diazonium ion:

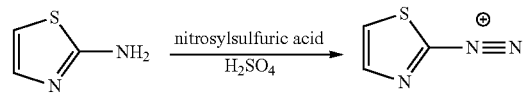 [SMILES: Nc1nccs1 ; "H2SO4" ; N#[N+]c1nccs1]

The reactive diazonium ion then enters into a double azo coupling reaction with dimeric aniline derivatives

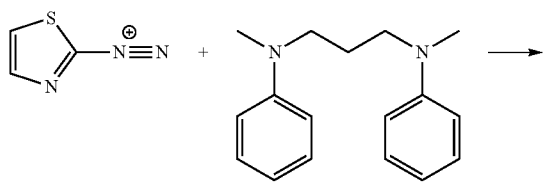

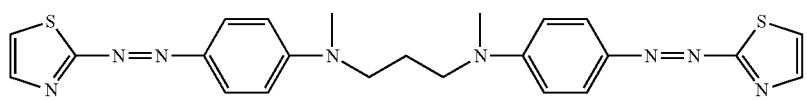

The neutral dimeric dye produced in the azo coupling reaction can then lastly be doubly quaternized with quaternization agents. The quaternization reaction is preferably carried out in a polar aprotic solvent (such as DMSO, DMF, etc.). For example, dimethyl sulfate, methyl iodide, or p-toluene sulfonate are possible quaternization agents.

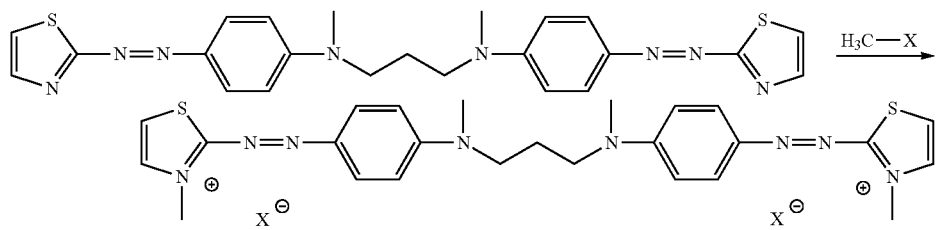

As second component (b) essential to various embodiments of the present disclosure, the agents for dyeing keratin fibers contain at least one anionic surfactant.

Surfactants are amphiphilic (bifunctional) compounds which consist of at least one hydrophobic and at least one hydrophilic molecule part. The hydrophobic group is preferably a hydrocarbon chain having 8-24 carbon atoms, which can be saturated or unsaturated, linear or branched. This $C_8$-$C_{24}$ alkyl chain is particularly preferably linear.

In the case of anionic surfactants, the hydrophilic molecule part comprises a negatively charged hydrophilic head group. The negatively charged hydrophilic head group can be, for example, a carboxylic acid group or the salt of a carboxylic acid group, a sulfonic acid group or the salt of the sulfonic acid group, a sulfuric acid ester grouping or the salt hereof, a phosphonic group or the salt of the phosphonic acid group, or a phosphoric acid ester grouping or the salt hereof The cosmetic agent according to an exemplary embodiment of the present disclosure usually comprises an aqueous carrier. The aforementioned hydrophilic head groups of the anionic surfactant, such as the carboxylic acid and the salts of the carboxylic acids, are present in aqueous solution in an equilibrium, the position of which is co-determined by the pH value of the agent. If, for example, a fatty acid is used as anionic surfactant, a small part of the fatty acid thus lies in aqueous solution in the form of the protonated fatty acid, whereas the majority of the fatty acid in aqueous solution is deprotonated and in this way is converted into the salt of the fatty acid. For this reason, the definition of an anionic surfactant also includes a surfactant having an acid group (still protonated).

An anionic surfactant (b) in the sense of the present disclosure does not contain any cationic groupings, i.e. zwitterionic surfactants are also included by the definition of an anionic surfactant.

Anionic surfactants according to an exemplary embodiment of the present disclosure are therefore characterized by the presence of a water-soluble-making anionic group, such as a carboxylate, sulfate, sulfonate, or phosphate group and a lipophilic alkyl group having approximately 8 to 30 C atoms. In addition, glycol or polyglycol ether groups, ester, ether and amide groups, and also hydroxyl groups can be contained in the molecule.

Typical examples of anionic surfactants are alkylbenzene sulfonates, alkane sulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monoglyceride(ether)sulfates, fatty acid amide(ether)sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates (in particular wheat-based plant products) and alkyl(ether)phosphates. Provided the anionic surfactants contain polyglycol ether chains, these can have a convention, but preferably a restricted homologue distribution.

Examples of anionic surfactants according to an exemplary embodiment of the present disclosure are, in each case in the form of the sodium, potassium and ammonium salts and also the mono-, di- and trialkanol ammonium salts having 2 to 4 C atoms in the alkanol group, linear and branched fatty acids having 8 to 30 C atoms (soaps), ether carboxylic acids of formula R—O—$(CH_2$—$CH_2$O$)_x$—$CH_2$—COOH, in which R is a linear alkyl group having 8 to 30 C atoms and x=0 or is 1 to 16, acyl sarcosides having 8 to 24 C atoms in the acyl group, acyl taurides having 8 to 24 C atoms in the acyl group, acyl isethionates having 8 to 24 C atoms in the acyl group, which are accessible by esterification of fatty acids with the sodium salt of 2-hydroxyethane sulfonic acid (isethionic acid). If fatty acids having 8 to 24 C atoms are used for this esterification, i.e. for example lauric, myristic, palmitic, or stearic acid or also technical fatty acid fractions, for example the $C_{12}$-$C_{18}$ fatty acid fraction obtainable from coconut fatty acid, the $C_{12}$-$C_{18}$ acylisethionates preferably suitable in accordance with the present disclosure are obtained, sulfosuccinic acid mono- and dialkyl esters having 8 to 24 C atoms in the alkyl group and sulfosuccinic acid monoalkyl poly oxyethyl esters having 8 to 24 C atoms in the alkyl group and 1 to 6 oxyethyl groups. Sulfosuccinic acid mono- and dialkyl esters can be produced by reacting maleic acid anhydride with a fatty alcohol having 8-24 C atoms to form maleic acid monoesters of the fatty alcohol and further reacting these with sodium sulfite to form sulfosuccinic acid esters. Particularly suitable sulfosuccinic acid esters derive from fatty alcohol fractions having 12-18 C atoms, as are accessible for example from coconut fatty acid or coconut fatty acid methyl esters by hydrogenation, linear alkane sulfonates having 8 to 24 C atoms, linear alpha-olefin sulfonates having 8 to 24 C atoms, alpha-sulfofatty acid methyl esters of fatty acids having 8 to 30 C atoms, alkyl sulfates and alkyl polyglycol sulfates of formula R—O$(CH_2$—$CH_2$O$)_x$—$OSO_3$H, in which R is a preferably linear alkyl group having 8 to 30 C atoms and x=0 or is 1 to 12, hydroxy sulfonates corresponding substantially to one of the two following formulas or mixtures thereof and also salts thereof, $CH_3$—$(CH_2)_y$-CHOH—$(CH_2)_p$-(CH—$SO_3$M)-$(CH_2)_z$—$CH_2$—O—$(CnH_{2n}O)_x$—H, and/or $CH_3$—$(CH_2)_y$-(CH—$SO_3$M)-$(CH_2)_p$-CHOH—$(CH_2)_z$—$CH_2$—O—$(C_nH_{2n}O)_x$—H, wherein in both formulas y and z=0 or integers from 1 to 18, p=0.1 or 2, and the sum (y+z+p) is a number from 12 to 18, x=0 or a number from 1 to 30, and n is an integer from 2 to 4 and M=H or an alkali, in particular sodium, potassium, lithium, alkaline earth, in particular magnesium, calcium, zinc and/or ammonium ion, which optionally can be substituted, in particular mono-, di-, tri- or tetraammonium ions with C1 to C4 alkyl, alkenyl or aryl groups, sulfated hydroxyalkyl polyethylene and/or hydroxyalkylene propylene glycol ethers of formula $R^1$—(CHOSO$_3$M)-CHR$^3$—(OCHR$^4$—CH$_2$)n=OR$^2$, with $R^1$, a linear alkyl group having 1 to 24 C atoms, $R^2$ for a linear or branched, saturated alkyl group having 1 to 24 C atoms, $R^3$ for hydrogen or a linear alkyl group having 1 to 24 C atoms, $R^4$ for hydrogen or a methyl group, and M for hydrogen, ammonium, alkylammonium, alkanolammonium, wherein the alkyl and alkanol groups each have 1 to 4 C atoms, or a metal atom selected from lithium, sodium, potassium, calcium or magnesium and n stands for a number in the range from 0 to 12 and also the total number of the C atoms contained in $R^1$ and $R^3$ is 2 to 44, sulfonates of unsaturated fatty acids having 8 to 24 C atoms and 1 to 6 double bonds, esters of tartaric acid and citric acid with alcohols, which represent addition products of approximately 2-15 molecules of ethylene oxide and/or propylene oxide with fatty alcohols having 8 to 22 C atoms, alkyl and/or alkenyl ether phosphates of formula $R^1(OCH_2CH_2)_n$—O—(PO—OX)—OR$^2$, in which $R^1$ preferably stands for an aliphatic hydrocarbon group having 8 to 30 carbon atoms, $R^2$ stands for hydrogen, a group $(CH_2CH_2O)_nR^2$ or X, n stands for numbers from 1 to 10, and X stands for hydrogen, an alkali or alkaline earth metal or $NR^3R^4R^5R^6$, with $R^3$ to $R^6$ independently of one another standing for hydrogen or a $C_1$ to $C_4$ hydrocarbon group, sulfated fatty acid alkylene glycol esters of formula $RCO(AlkO)_nSO_3M$, in which RCO-stands for a linear or branched, aliphatic, saturated and/or unsaturated acyl group having 6 to 22 C atoms, Alk stands for $CH_2CH_2$, $CHCH_3CH_2$ and/or $CH_2CHCH_3$, n stands for numbers from 0.5 to 5, and M stands for a metal, such as alkali metal, in particular sodium, potassium, lithium, alkaline earth metal, in particular magnesium, calcium, zinc, or ammonium ion, such as $^+NR^3R^4R^5R^6$, with $R^3$ to $R^6$ independently of one another standing for hydrogen or a C1 to C4 hydrocarbon group, monoglyceride sulfates and monoglyceride ether sulfates of formula $R^8OC$—$(OCH_2CH_2)_x$—$OCH_2$—[CHO$(CH_2CH_2O)_yH]$—$CH_2O(CH_2CH_2O)_z$—$SO_3X$, in which $R^8CO$ stands for a linear or branched acyl group having 6 to 22 carbon atoms, x, y and z in sum stand for 0 and for numbers from 1 to 30, preferably 2 to 10, and X stands for an alkali or alkaline earth metal. Typical examples of monoglyceride(ether)sulfates that are suitable in the sense of the present disclosure are the reaction products of lauric acid monoglyceride, coconut fatty acid monoglyceride, palmitic acid monoglyceride, stearic acid monoglyceride, oleic acid monoglyceride, and tallow fatty acid monoglyceride and the ethylene oxide adducts thereof with sulfur trioxide or chlorosulfonic acid in the form of the sodium salts thereof. Monoglyceride sulfates are preferably used in which $R^8CO$ stands for a linear acyl group having 8 to 18 carbon atoms, amide ether carboxylic acids, $R^1$—CO—NR$^2$—CH$_2$CH$_2$—O—(CH$_2$CH$_2$O)$_n$CH$_2$COOM, with $R^1$ as a straight-chained or branched alkyl or alkenyl group with a number of carbon atoms in the chain from 2 to 30, n stands for an integer from 1 to 20, and $R^2$ stands for hydrogen, a methyl, ethyl, propyl, isopropyl, n-butyl, t-butyl, or isobutyl group, and M stands for hydrogen or a metal such as alkali metal, in particular sodium, potassium, lithium, alkaline earth metal, in particular magnesium, calcium, zinc, or an ammonium ion, such as $^+NR^3R^4R^5R^6$, with $R^3$ to $R^6$ independently of one another standing for hydrogen or a C1 to C4 hydrocarbon group. Such products are obtainable for example from the company Chem-Y under the product name Akypo®, and acyl glutamates of formula XOOC—CH2CH2CH(C(NH)OR)—COOX, in which RCO stands for a linear or branched acyl group having 6 to 22 carbon atoms and 0 and/or 1, 2 or 3 double bonds, and X stands for hydrogen, an alkali and/or alkaline earth metal, ammonium, alkylammonium, alkanolammonium, or glucammonium.

The treatment of keratin fibers with agents that contained (a) at least one direct dye of formula (I) and (b) at least one anionic surfactant led to intense colorings in attractive, pure blue nuances without red component. Here, it has surprisingly been found that the color absorption capability could be optimized further still by use of one or more specific anionic surfactants. Particularly intense blue colorings were obtained if the dyes (a) of formula (I) with at least one anionic surfactant (b) from the group of linear and branched fatty acids having 8 to 30 C atoms,
ether carboxylic acids of formula R—O—(CH$_2$—CH$_2$O)$_x$—CH$_2$—COOH, in which R is a linear alkyl group having 8 to 30 C atoms and x=0 or 1 to 16,
acyl sarcosides having 8 to 24 C atoms in the acyl group,
acyl taurides having 8 to 24 C atoms in the acyl group,
acyl isethionates having 8 to 24 C atoms in the acyl group, which are accessible by esterification of fatty acids with the sodium salt of the 2-hydroxyethane sulfonic acid (isethionic acid). If fatty acids having 8 to 24 C atoms are used for this esterification, i.e. for example lauric, myristic, palmitic, or stearic acid or also technical fatty acid fractions, for example the $C_{12}$-$C_{18}$ fatty acid fraction obtainable from coconut fatty acid, the $C_{12}$-$C_{18}$ acylisethionates preferably suitable in accordance with the present disclosure are obtained.

amide ether carboxylic acids, $R^1$—CO—NR$^2$—CH$_2$CH$_2$—O—(CH$_2$CH$_2$O)$_n$CH$_2$COOM, with $R^1$ as a straight-chained or branched alkyl or alkenyl group with a number of carbon atoms in the chain from 2 to 30, n stands for an integer from 1 to 20, and $R^2$ stands for hydrogen, a methyl, ethyl, propyl, isopropyl, n-butyl, t-butyl, or isobutyl group, and M stands for hydrogen or a metal such as alkali metal, in particular sodium, potassium, lithium, alkaline earth metal, in particular magnesium, calcium, zinc, or an ammonium ion, such as $^+NR^3R^4R^5R^6$, with $R^3$ to $R^6$ independently of one another standing for hydrogen or a C1 to C4 hydrocarbon group. Such products are obtainable for example from the company Chem-Y under the product name Akypo®, and acyl glutamates of formula XOOC—CH2CH2CH(C(NH)OR)—COOX, in which RCO stands for a linear or branched acyl group having 6 to 22 carbon atoms and 0 and/or 1, 2 or 3 double bonds, and X stands for hydrogen, an alkali and/or alkaline earth metal, ammonium, alkylammonium, alkanolammonium, or glucammonium.

In a particularly preferred embodiment an agent according to the present disclosure is therefore characterized in that it contains (b) at least one anionic surfactant selected from the linear and branched fatty acids having 8 to 30 C atoms,
ether carboxylic acids of formula R—O—(CH$_2$—CH$_2$O)$_x$—CH$_2$—COOM, in which
R stands for a linear alkyl group having 8 to 30 C atoms,
x stands for an integer from 0 to 16,
M stands for hydrogen or a metal such as alkali metal, in particular sodium, potassium, lithium, alkaline earth metal, in particular magnesium, calcium, zinc, or an ammonium ion (NH4$^+$), acyl sarcosides having 8 to 24 C atoms in the acyl group,
acyl taurides having 8 to 24 C atoms in the acyl group,
acyl isethionates having 8 to 24 C atoms in the acyl group,
which are accessible by esterification of $C_8$-$C_{24}$ fatty acids with the sodium salt of the 2-hydroxyethane sulfonic acid (isethionic acid),
amide ether carboxylic acids, $R^1$—CO—$NR^2$—$CH_2CH_2$—O—$(CH_2CH_2O)_y CH_2COOM$, wherein
$R^1$ stands for a C2-C30 alkyl group,
y stands for an integer from 1 to 20,
$R^2$ stands for hydrogen, a methyl, ethyl, propyl, isopropyl, n-butyl, t-butyl or iso-butyl group, and
M stands for hydrogen or a metal, such as alkali metal, in particular sodium, potassium, lithium, alkaline earth metal, in particular magnesium, calcium, zinc, or an ammonium ion (NH4+).

A particularly good color absorption capability could be observed if at least one ether carboxylic acid of formula R—O—(CH2-CH2O)x-CH2-COOH or salt thereof was used as anionic surfactant (b). The use of (optionally ethoxylated) ether carboxylic acids is therefore explicitly very particularly preferred.

In an explicitly very particularly preferred embodiment, an agent according to the present disclosure is therefore characterized in that it contains, as anionic surfactant (b), at least one ether carboxylic acid of formula (B1)

R—O—(CH$_2$—CH$_2$O)x-CH2-COOM     (B1)

wherein
R stands for a linear alkyl group having 8 to 30 C atoms,
x stands for an integer from 0 to 16,
M stands for hydrogen or a metal such as alkali metal, in particular sodium, potassium, lithium, an alkaline earth metal, in particular ½ magnesium, ½ calcium, ½ zinc, or an ammonium ion (NH4+).

Furthermore, x preferably stands for the numbers 5, 6 or 7.

In a further very particularly preferred embodiment, an agent according to the present disclosure is therefore characterized in that it contains, as anionic surfactant (b), at least one ether carboxylic acid of formula (B1)

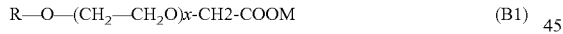

R—O—(CH$_2$—CH$_2$O)x-CH2-COOM     (B1)

wherein
R stands for a linear alkyl group having 8 to 30 C atoms,
x stands for an integer from 5 to 11,
M stands for hydrogen or a metal such as alkali metal, in particular sodium, potassium, lithium, an alkaline earth metal, in particular ½ magnesium, ½ calcium, ½ zinc, or an ammonium ion (NH4+).

Very particularly preferred anionic surfactants of formula (B1) are obtainable for example under the trade names
Akypo Soft 45 HP from the company Kao (Sodium Laureth-6 Carboxylate)
Akypo Soft 45 NV from the company Kao (Sodium Laureth-5 Carboxylate)
Akypo RLM 100 NV from the company Kao (Sodium Laureth-11 Carboxylate).

The agents according to an exemplary embodiment of the present disclosure for dyeing keratin fibers preferably contain one or more anionic surfactants (b) in a total amount of from about 0.05 to about 4.5% by weight, preferably from about 0.1 to about 3.1% by weight, more preferably from about 0.15 to about 2.5% by weight, and very particularly preferably from about 0.2 to about 0.9% by weight. Here, the values in % by weight relate to the total amount of all anionic surfactants (b), and are set in relation to the total amount of the dye.

In a further particularly preferred embodiment, an agent according to the present disclosure for dyeing keratin fibers is therefore characterized in that it contains in relation to the total weight of the agent one or more anionic surfactants (b) in a total amount of from about 0.05 to about 4.5% by weight, preferably from about 0.1 to about 3.1% by weight, more preferably from about 0.15 to about 2.5% by weight, and very particularly preferably from about 0.2 to about 0.9% by weight.

As previously described, it has been found that the color absorption capability of the direct dyes of formula (I) can be influenced by varying the anionic surfactant(s) (b).

In general, the color absorption can be improved by use of at least one anionic surfactant. The use of at least one (optionally ethoxylated) ether carboxylic acid and/or salt thereof as described in formula (B1) has proven in this context to be particularly advantageous. In this context it was observed that the keratin fibers can be colored in particular in intense blue nuances if the ether carboxylic acid(s) (and/or salts thereof) was/were contained as the primary anionic surfactant in the agent according to an exemplary embodiment of the present disclosure.

In other words, the color results were particularly intense when the agents according to an exemplary embodiment of the present disclosure contained one or more ether carboxylic acids of formula (B1) and when, in addition, all further used anionic surfactants were present only in smaller amounts. The use of the ether carboxylic acid(s) of formula (B1) as main surfactant can be quantified by specification of a ratio by weight which sets the total amount of the anionic surfactants of formula (B1) contained in the agent in relation to the total amount of all anionic surfactants (b) contained in the agent.

In a further particularly preferred embodiment, an agent according to the present disclosure for dyeing keratin fibers is therefore characterized in that the ratio by weight of all anionic surfactants of formula (B1) contained in the agent to the total amount of the anionic surfactants contained in the agent lies at a value of 0.5, preferably of 0.6, more preferably of 0.75, and particularly preferably of 0.9.

Example

An agent for dyeing keratin fibers contains:
(a) 1.0 g of 3-methyl-2-[2-(4-{[3-({4-[2-(3-methyl-1,3-thiazol-3-ium-2-yl)diazen-1-yl]phenyl}amino)propyl]amino}phenyl)diazen-1-yl]-1,3-thiazol-3-ium tetrachlorozincate
(b) 0.23 g of sodium laureth-6 carboxylate (B1) and
(b) 0.10 g of sodium laureth sulfate (2 EO).

The ratio by weight of all anionic surfactants of formula (B1) contained in the agent to the total amount of the anionic surfactants contained in the agent lies at a value of [0/23/(0.23+0.1)]=0.70

Example

An agent for dyeing keratin fibers contains:
(a) 1.0 g of 3-methyl-2-[2-(4-{[3-({4-[2-(3-methyl-1,3-thiazol-3-ium-2-yl)diazen-1-yl]phenyl}amino)propyl]amino}phenyl)diazen-1-yl]-1,3-thiazol-3-ium tetrachlorozincate
(b) 0.23 g of sodium laureth-6 carboxylate (B1) and
no further anionic surfactants.

The ratio by weight of all anionic surfactants of formula (B1) in the agent to the total amount of the anionic surfactants contained in the agent lies at a value of [0.23/0.23]=1.0

Furthermore, the agents according to an exemplary embodiment of the present disclosure can also contain one or more cationic surfactants. Cationic surfactants are understood to mean surfactants, i.e. surface-active compounds, with in each case one or more positive charges. Cationic surfactants contain exclusively positive charges. These surfactants are usually constructed from a hydrophobic part and a hydrophilic head group, wherein the hydrophobic part generally consists of a hydrocarbon skeleton (for example consisting of one or two linear or branched alkyl chains), and the positive charge(s) is/are localized in the hydrophilic head group. Cationic surfactants adsorb at interfaces and aggregate in aqueous solution above the critical micelle formation concentration to form positively charged micelles.

Examples of cationic surfactants are quaternary ammonium compounds, which as hydrophobic groups can carry one or two alkyl chains having a chain length of 8 to 28 C atoms quaternary phosphonium salts, substituted with one or more alkyl chains having a chain length of 8 to 28 C atoms, or tertiary sulfonium salts.

Furthermore, the cationic charge also in the form of an onium structure can be part of a heterocyclic ring (for example of an imidazolium ring or a pyridinium ring).

Besides the functional unit carried by the cationic charge, the cationic surfactant can also contain further uncharged functional groups, which is the case for example when it comes to esterquats.

Suitable cationic surfactants of this type are for example physiologically acceptable salts of N,N,N-trimethyl-1-hexadecanaminium, in particular N,N,N-trimethyl-1-hexadecanaminium chloride, which is also sold under the trade name Dehyquart A-CA.

A further suitable cationic surfactant is a physiologically acceptable salt of dimethyl distearyl dimethyl ammonium, particularly preferably dimethyl distearyl ammonium chloride.

Further cationic surfactants can be selected from the group of cationic imidazolium compounds.

The agent according to an exemplary embodiment of the present disclosure can contain the cationic surfactant(s) in a total amount of from about 0.1 to about 4.8% by weight, preferably from about 0.2 to about 2.4% by weight, more preferably from about 0.3 to about 1.8% by weight, in relation to the total weight of the agent.

It has also proven to be advantageous if the agents contain further, non-ionogenic surface-active substances. Preferred non-ionic surfactants have proven to be alkyl polyglycosides and alkylene oxide addition products with fatty alcohols and fatty acids each having 2 to 30 mol ethylene oxide per mol fatty alcohol or fatty acid. Preparations having excellent properties are also obtained if they contain fatty acid esters of ethoxylated glycerol as non-ionic surfactants.

In a further preferred embodiment the agents according to the present disclosure contain, in addition to the compound of formula (I), additionally at least one further direct dye. The attainable nuance spectrum can be extended by the combination with further cationic direct dyes, and the color properties can be improved further still.

Direct dyes can be divided into anionic, cationic, and non-ionic direct dyes.

The direct dyes are preferably selected from the cationic direct dyes, since these are highly compatible with the dyes of general formula (I).

In a further particularly preferred embodiment an agent according to the present disclosure is characterized in that it additionally contains at least one further cationic direct dye which is different from the dyes of formula (I).

One or more dyes from the group Basic Yellow 87, Basic Orange 31, Basic Red 51, Basic Violet 2, and Cationic Blue 347 have proven to be particularly compatible.

The dyes of formula (I) comprising the cationic azo dyes Basic Orange 31 and Basic Red 51 has proven to be very particularly compatible. Apart from purely yellow nuances, nuances in the entire color spectrum can be produced by combining a dye of formula (I) with Basic Orange 31 and/or Basic Red 51.

In a further particularly preferred embodiment an agent according to the present disclosure is characterized in that it additionally contains Basic Orange 31 and/or Basic red 51.

However, the agent according to an exemplary embodiment of the present disclosure can also additionally contain at least one non-ionic direct dye. This can be selected from the group HC Yellow 2, HC Yellow 4, HC Yellow 5, HC Yellow 6, HC Yellow 12, HC Orange 1, Disperse Orange 3, HC Red 1, HC Red 3, HC Red, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

In addition, anionic direct dyes which are known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol blue and Tetrabromophenol blue can be contained. The agents according to an exemplary embodiment of the present disclosure can furthermore also be used together with oxidation dyes. Such oxidation dyes additionally contain at least one oxidation dye precursor, preferably at least one oxidation dye precursor of the developer type and at least one oxidation precursor of the coupler type. Particularly suitable oxidation precursors of the developer type are selected here from at least one compound from the group that is formed from p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methyl-phenyl)-N-[3-(1H-imidazol-1-yl)propyl]amine, N,N'-bis-(2-hydroxyethyl)-N,N'-bis-(4-aminophenyl)-1,3-diamino-propan-2-ol, bis-(2-hydroxy-5-aminophenyl) methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl) phenol, 4,5- diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and physiologically acceptable salts thereof.

Particularly suitable oxidation precursors of the coupler type are selected here from the group formed from 3-aminophenol, 5-amino-2-methylphenol, 3-amino-2-chloro-6-methylphenol, 2-hydroxy-4-aminophenoxy ethanol, 5-amino-4-chloro-2-methylphenol, 5-(2-hydroxyethyl)-amino-2-methyl phenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl) amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindol, 6-hydroxyindol, 7-hydroxyindol, 4-hydroxyindolin, 6-hydroxyindolin, 7-hydroxyindolin or mixtures of these compounds or the physiologically acceptable salts thereof.

The additional direct dyes, developer components and coupler components are in each case used preferably in a proportion of from about 0.0001 to about 5.0% by weight, preferably about 0.001 to about 3.5% by weight, in each case in relation to the ready-to-use agent. Here, developer components and coupler components are used generally in approximately molar amounts relative to one another. If the molar use has also proven to be expedient, a certain excess of individual oxidation precursors is not disadvantageous, and therefore developer components and coupler components can be in a molar ratio of from about 1 to 0.5 to about 1 to 3, in particular about 1 to 1 to about 1 to 2.

If the coloring with the direct dyes of formula (I) according to an exemplary embodiment of the present disclosure and an oxidative lightening of the keratin fibers is performed in one step, the agents according to the embodiment additionally contain an oxidizing agent, preferably hydrogen peroxide and/or one of the solid addition products thereof with organic or inorganic compounds.

In a preferred embodiment, hydrogen peroxide itself is used as aqueous solution. The concentration of a hydrogen peroxide solution in the agent according to the embodiment is determined on the one hand by the legal stipulations and on the other hand by the desired effect; about 6 to about 12% by weight solutions in water are preferably used. ready-to-use agents forming the first subject of an exemplary embodiment that are preferred in accordance with the present disclosure are characterized in that they contain, in relation to the total weight of the ready-to-use agent, about 0.5 to about 20% by weight, preferably about 1 to about 12.5% by weight, particularly preferably about 2.5 to about 10% by weight, and in particular about 3 to about 6% by weight of hydrogen peroxide, in each case in relation to the total weight of the agent.

In a further particularly preferred embodiment, an agent according to the present disclosure is characterized in that it contains in relation to the total weight of the agent about 0.5 to about 12.5% by weight, preferably about 2.5 to about 10% by weight, and in particular about 3 to about 6% by weight of hydrogen peroxide.

In order to attain an intensified lightening and bleaching effect, the agent can also contain at least one peroxy salt. Suitable peroxy salts are inorganic peroxy compounds, preferably selected from the group formed from ammonium peroxydisulfate, alkali metal peroxydisulfates, ammonium peroxymonosulfate, alkali metal peroxymonosulfates, alkali metal peroxydiphosphates, and alkaline earth metal peroxides. Peroxydisulfates are particularly preferred, in particular ammonium peroxydisulfate, potassium peroxydisulfate, and sodium peroxydisulfate.

In a further particularly preferred embodiment an agent according to the present disclosure is characterized in that it additionally contains at least one persulfate from the group ammonium peroxydisulfate, potassium peroxydisulfate, and sodium peroxydisulfate.

The persulfates are each contained in the agent according to an exemplary embodiment of the present disclosure in an amount of from about 0.5 to about 20.5 by weight, preferably about 1 to about 12.5% by weight, particularly preferably about 2.5 to about 10% by weight, and in particular about 3 to about 6% by weight, in relation to the total weight of the ready-to-use agent.

The colorant and/or matting agent can contain further bleaching power intensifiers in order to intensify the bleaching effect, such as tetraacetylethylenediamine (TAED), 1,5-diacetyl-2,4-dioxo-hexahydro-1,3,5-triazine (DADHT), tetraacetyl glycoluril (TAGU), N-nonanoyl succinimide (NOSI), n-nonanoyl oxybenzenesulfonate or isononanoyl oxybenzenesulfonate (n- or iso-NOBS), phthalic acid anhydride, triacetin, ethylene glycol diacetate and 2,5-diacetoxy-2,5-dihydrofuran, and also carbonate salts or hydrogen carbonate salts, in particular ammonium hydrogen carbonate, ammonium carbonate, sodium hydrogen carbonate, disodium carbonate, potassium hydrogen carbonate, dipotassium carbonate, and calcium carbonate, and nitrogen-containing heterocyclic bleaching power intensifiers, such as 4-acetyl-1-methylpyridinium-p-toluenesulfonate, 2-acetyl-1-methylpyridinium-p-toluenesulfonate, and N-methyl-3,4-dihydroisoquinolinium-p-toluenesulfonate.

In order to further increase the lightening, the composition according to an exemplary embodiment of the present disclosure can additionally be mixed with at least one SiO2 compound, such as silica or silicates, in particular waterglasses. In accordance with an exemplary embodiment of the present disclosure, it can be preferred to use the SiO2 compounds in amounts of from about 0.05% by weight to about 15% by weight, particularly preferably in amounts from about 0.15% by weight to about 10% by weight, and very particularly preferably in amounts from about 0.2% by weight to about 5% by weight, in each case in relation to the anhydrous composition. The specified amounts in each case reflect the content of the SiO2 compounds (without the water component thereof) in the agents.

The colorants can also contain additional active substances, auxiliaries and additives in order to improve the coloring power and set further desirable properties of the agent.

The colorants are preferably provided as a liquid preparation and the agents therefore optionally additionally are mixed with a further surface-active substance, wherein such surface-active substances are referred to as surfactants or as emulsifiers depending on the field of application: They are preferably selected from anionic, zwitterionic, amphoteric and non-ionic surfactants and emulsifiers.

The colorants according to an exemplary embodiment of the present disclosure can contain further auxiliaries and additives. It has thus proven advantageous if the agent contains at least one thickener. In principle, there are no limitations in respect of this thickener. Both organic and purely inorganic thickeners can be used.

Suitable thickeners are anionic, synthetic polymers;

cationic, synthetic polymers;

naturally occurring thickeners, such as non-ionic guar gum, scleroglucan gum, or xanthan gum, gum arabic, ghatti gum, karaya gum, tragacanth gum, carrageenan gum, agar agar, locust bean gum, pectins, alginates, starch fractions, and derivatives such as amylose, amylopectin and dextrins and also cellulose derivatives, such as methyl cellulose, carboxy alkyl celluloses and hydroxy alkyl cellulose;

non-ionic fully synthetic polymers, such as polyvinyl alcohol or polyvinyl pyrrolidone; and inorganic thickeners, in particular sheet silicates, such as bentonite, in particular smectites, such as montmorillonite or hectorite.

Coloring processes on keratin fibers are usually performed in an alkaline environment. In order to protect the keratin fibers and also the skin to the greatest possible extent, however, it is not desirable to set a pH value that is too high. Thus, it is preferred if the pH value of the ready-to-use agent is between about 7 and about 11, in particular between about 8 and about 10.5. The pH values in the sense of the present disclosure are pH values which have been measured at a temperature of about 22° C.

The alkalizing agents that can be used in accordance with the present disclosure to set the preferred pH value can be selected from the group formed from ammonia, alkanolamines, basic amino acids, and inorganic alkalizing agents, such as alkaline (earth) metal hydroxides, alkaline (earth) metal silicates, alkaline (earth) metal phosphates, and alkaline (earth) metal hydrogen phosphates. Preferred inorganic alkalizing agents are magnesium carbonate, sodium hydroxide, potassium hydroxide, sodium silicate, and sodium metasilicate. Organic alkalizing agents usable in accordance with the present disclosure are preferably selected from monoethanolamine, 2-amino-2-methylpropanol, and triethanolamine. The basic amino acids usable as alkalizing agents according to an exemplary embodiment of the present disclosure are preferably selected from the group formed from arginine, lysine, ornithine, and histidine, particularly preferably arginine. However, it has been found within the scope of the investigations for the present disclosure that agents which are preferred in accordance with the present disclosure are also characterized in that they additionally contain an organic alkalizing agent. One embodiment of the first subject matter of the present disclosure is characterized in that the agent additionally contains at least one alkalizing agent which is selected from the group formed from ammonia, alkanolamines, and basic amino acids, in particular from ammonia, monoethanolamine, and arginine or acceptable salts thereof.

It has also proven to be advantageous if the colorants, in particular if they additionally contain hydrogen peroxide, contain at least one stabilizer or complexing agent. Particularly preferred stabilizers are phenacetin, alkali benzoates (sodium benzoate) and salicylic acid. All complexing agents of the prior art can also be used. Complexing agents which are preferred in accordance with the present disclosure are nitrogen-containing polycarboxylic acids, in particular EDTA and EDDS, and phosphonates, in particular 1-hydroxyethane-1-1-diphosphonate (HEDP) and/or ethylenediamine tetramethylene phosphonate (EDTMP) and/or diethylene triamine pentamethylene phosphonate (DTPMP) or sodium salts thereof.

Furthermore, the agents according to an exemplary embodiment of the present disclosure can contain further active substances, auxiliaries and additives, such as non-ionic polymers, such as vinylpyrrolidinone/vinylacrylate copolymers, polyvinylpyrrolidinone, vinylpyrrolidinone/vinylacetate copolymers, polyethylene glycols and polysiloxanes; additional silicones such as volatile or non-volatile, straight-chain, branched or cyclic, cross-linked or uncross-linked polyalkyl siloxanes (such as dimethicones or cyclomethicones), polyaryl siloxanes and/or polyalkyl aryl siloxanes, in particular polysiloxanes with organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers such as quaternized cellulose ethers, polysiloxanes having quaternary groups, dimethyldiallyl ammonium chloride polymers, acrylamide-dimethyldiallyl ammonium chloride copolymers, dimethylaminoethyl methacrylate-vinylpyrrolidinone copolymers quaternized with diethyl sulfate, vinylpyrrolidinone-imidazolinium-methochloride copolymers and quaternized polyvinyl alcohol; zwitterionic and amphoteric polymers; anionic polymers such as polyacrylic acids or cross-linked polyacrylic acids; structuring agents such as glucose, maleic acid and lactic acid, hair-conditioning compounds such as phospholipids, for example lecithin and cephalins; perfume oils, dimethyl isosorbide and cyclodextrins; fiber structure-improving active substances, in particular mono-, di- and oligosaccharides such as glucose, galactose, fructose, fruit sugars and lactose; dyes for coloring the agent; anti-dandruff active agents such as piroctone olamine, zinc omadine and climbazole; amino acids and oligopeptides; protein hydrolysates of animal and/or plant origin as well as those in the form of their fatty acid condensation products or optionally anionically or cationically modified derivatives thereof; vegetable oils; light stabilizers and UV blockers; active agents such as panthenol, pantothenic acid, pantolactone, allantoin, pyrrolidinone carboxylic acids and salts thereof as well as bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; pigments, as well as propellants such as propane-butane mixtures, N2O, dimethyl ether, CO2 and air.

These further substances will be selected by a person skilled in the art in accordance with the desired properties of the agents. With regard to further optional components and the used amounts of these components, reference is made expressly to the relevant handbooks known to a person skilled in the art. The additional active substances and auxiliaries are used in the agents according to an exemplary embodiment of the present disclosure preferably in amounts of, in each case, about 0.0001 to about 25% by weight, in particular from about 0.0005 to about 15% by weight, in each case in relation to the total weight of the ready-to-use mixture.

Keratin fibers can be dyed in particularly attractive and intense blue tones using the colorants which contain the direct dyes of general formula (I) according to an exemplary embodiment of the present disclosure. The dyes of general formula (I) are cationic dimeric azo dyes. Here, it has surprisingly been found that the color intensity of cationic azo dyes can be increased further still by adding one or more anionic surfactants (b) of formula (B1),

R—O—(CH2-CH2O)x-CH2-COOM (B1)

wherein
R stands for a linear alkyl group having 8 to 30 C atoms,
x stands for an integer from 0 to 16,
M stands for hydrogen or a metal such as alkali metal, in particular sodium, potassium, lithium, an alkaline earth metal, in particular ½ magnesium, ½ calcium, ½ zinc, or an ammonium ion (NH4+).

A second subject of the present disclosure is therefore the use of one or more anionic surfactants (b) of formula (B1)

R—O—(CH2-CH2O)x-CH2-COOM (B1)

wherein
R stands for a linear alkyl group having 8 to 30 C atoms,
x stands for an integer from 0 to 16,
M stands for hydrogen or a metal such as alkali metal, in particular sodium, potassium, lithium, an alkaline earth metal, in particular ½ magnesium, ½ calcium, ½ zinc, or an ammonium ion (NH4+),
for improving the color absorption capability of cationic azo dyes onto keratin fibers.

The improvement of the color absorption capability is understood in this context to mean that the dyes diffuse in increasing number or in an intensified manner into the keratin fibers, which leads to colorings of greater color intensity. The increased color intensity can be detected either visually by observation under a daylight lamp or by colorimetric measurement (determination of the lab values).

Suitable cationic azo dyes are, for example the dyes Basic Yellow, Basic Orange 31, and Basic Red 51.

The intensification of the color absorption by the anionic surfactants of formula (B1) in principle functions with all cationic azo dyes. However, the color absorption of the dyes of general formula (I) can be improved particularly well by adding the anionic surfactants of formula (B1).

A further subject of the present disclosure is therefore the use of one or more anionic surfactants (b) of formula (B1)

R—O—(CH2-CH2O)x-CH2-COOM (B1)

wherein
R stands for a linear alkyl group having 8 to 30 C atoms,
x stands for an integer from 0 to 16,
M stands for hydrogen or a metal such as alkali metal, in particular sodium, potassium, lithium, an alkaline earth metal, in particular ½ magnesium, ½ calcium, ½ zinc, or an ammonium ion (NH4+),
for improving the color absorption capability of direct dyes of general formula (I), as are disclosed in the above description of the first subject matter of the present disclosure, onto keratin fibers.

The agents of the first subject matter of the present disclosure can be used in methods for dyeing and also in methods for the simultaneous bleaching or lightening and dyeing of human hair.

The agents according to an exemplary embodiment of the present disclosure can be formulated as one-component agents or as multi-component agents, such as two-component agents or three-component agents, and can be used accordingly. A separation into multi-component systems lends itself in particular where incompatibilities between the ingredients are anticipated or feared; in such systems, the agent to be used is produced by the user directly before use, by mixing the components.

The agent according to an exemplary embodiment of the present disclosure for changing the color of keratin fibers is always understood to be the ready-to-use agent.

If the agent according to an exemplary embodiment of the present disclosure is provided to the user in the form of a one-component agent, the ready-to-use agent then does not first have to produced, but can be removed directly from the container in which it was packaged and applied to the keratin fibers.

Bleaching agents, however, are usually two-component products in which an oxidizing agent-containing component (A1) is mixed shortly before use with a (alkalizing) agent (A2), and this ready-to-use mixture is then applied to the hair.

In this case the agent according to an exemplary embodiment of the present disclosure is the ready-to-use agent which was produced shortly before use by mixing (A1) and (A2).

Here, the direct dyes of general formula (I) can be provided in the component (A1) (i.e. together with the oxidizing agent) or in the component (A2) (together with the alkalizing agent).

It is also possible and in accordance with the present disclosure if the ready-to-use agent is produced shortly before the application to the human hair by mixing 3 components, wherein
the component (A1) contains at least one direct dye of general formula (I) and at least one alkalizing agent
the component (A2) contains at least a first oxidizing agent (for example hydrogen peroxide) and
the component (A3) contains at least one second oxidizing agent (for example one or more peroxydisulfates).

During the reaction time of the agent on the fibers it can be advantageous to assist the lightening process or matting process by supplying heat. The supply of heat can be provided by an external heat source, such as hot air of a hot air fan, and, in particular in the case of a lightening of hair on living beings, by means of the body temperature of the living being. In the latter case, the treated party is usually covered by a hood. A reaction phase at room temperature is also in accordance with the present disclosure. In particular, the temperature during the reaction time is between about 20° C. and about 40° C., in particular between about 25° C. and about 38° C. After the end of the reaction time, the remaining coloring preparation is rinsed from the hair using water or a cleansing agent. Here, commercially available shampoos in particular can serve as cleansing agent, wherein in particular the cleansing agent can be omitted and the rinsing process can be performed with water if the lightening agent has a strong surfactant carrier.

That which has been said in relation to the agents according to the present disclosure applies, mutatis mutandis, in relation to further preferred embodiments of the uses according to the present disclosure.

EXAMPLES

Direct dye 1: 3-methyl-2-(2-{4-[methyl({3-[methyl({4-[2-(3-methyl-1,3-thiazol-3-ium-2-yl)diazen-1-yl]phenyl})

amino]propyl})amino]phenyl}diazen-1-yl)-1,3-thiazol-3-ium, di(methyl sulfate) (DZ 1, according to an exemplary embodiment of the present disclosure)

The dye DZ 1 was synthesized in accordance with a method as described in documents WO 2002/100369 A2.

2-aminothiazole and N,N'-dimethyl-N,N'-diphenyl-propan-1,3-diamine were used as reactants (azo coupling reaction in aqueous, sulfuric solution with nitrosylsulfuric acid). The neutral dye created in this azo coupling reaction was then quaternized (for example with the quaternization agent dimethyl sulfate in a polar, aprotic solvent, such as dimethyl formamide or dimethyl sulfoxide).

DZ 1 (According to an Exemplary Embodiment of the Present Disclosure)

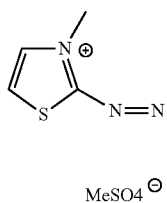
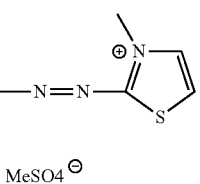

MeSO4⁻   MeSO4⁻

Comparative Example

Direct dye 2: 3-methyl-2-(2-{4-[methyl({2-[methyl({4-[2-(3-methyl-1,3-thiazol-3-ium-2-yl)diazen-1-yl]phenyl})amino]ethyl})amino]phenyl}diazen-1-yl)-1,3-thiazol-3-ium di(methyl sulfate) (DZ 2, comparison). The dye DZ 2 was synthesized in accordance with a method as described in documents WO 2002/100369 A2 and U.S. Pat. No. 3,291,788.

2-aminothiazole and N,N'-dimethyl-N,N'-diphenyl-ethan-1,3-diamine were used as reactants (azo coupling reaction in aqueous, sulfuric solution with nitrosylsulfuric acid). The dye created in this azo coupling reaction was then quaternized (for example with a quaternization agent such as dimethyl sulfate in a polar, aprotic solvent, such as dimethyl formamide or dimethyl sulfoxide).

DZ 2 (Comparison):

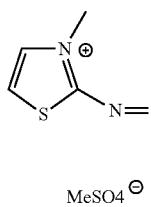
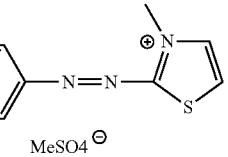

MeSO4⁻   MeSO4⁻

Coloring Examples

Formulations

The following coloring creams were produced (all values in % by weight, active substance)

|  | V1 | V2 | E1 | E2 |
|---|---|---|---|---|
| Cetearyl alcohol (C16/C18 fatty alcohol) | 1.0 | 1.0 | 1.0 | 1.0 |
| Coconut alcohol (C12/C18 fatty alcohol) | 1.0 | 1.0 | 1.0 | 1.0 |

-continued

|  | V1 | V2 | E1 | E2 |
|---|---|---|---|---|
| Methyl paraben | 0.1 | 0.1 | 0.1 | 0.1 |
| Propyl paraben | 0.1 | 0.1 | 0.1 | 0.1 |
| Sodium laureth-5 carboxylate | — | 1.0 | — | 1.0 |
| Sodium laureth sulfate (2 EO) | 1.0 | — | 1.0 | — |
| DZ 1 (according to an exemplary embodiment of the present disclosure) | — | — | 1.0 | 1.0 |
| DZ 2 (comparison) | 1.0 | 1.0 | — | — |
| Ammonium sulfate | 1.0 | 1.0 | 1.0 | 1.0 |
| Water | to 100 | to 100 | to 100 | to 100 |

The first five components were melted together. This melt was emulsified with hot water, then the dye pre-dissolved in propylene glycol was added and the ammonium sulfate solution was added. The specified pH value was adjusted with ammonia, then the mixture was filled to 100 g with water.

Colorations

In each case 1.8 g of the coloring cream was applied to a strand of human hair 6 cm long (Kerling Euro natural hair, 80% greyed) and was left there for 30 minutes at 30° C. Once the action time had elapsed, the hair was rinsed, washed using a conventional hair shampoo, and then dried. After drying, the coloration and the color intensity of the strands were assessed visually under a daylight lamp.

|  | Formulation | pH value | Color nuance | Color intensity |
|---|---|---|---|---|
| V1 | DZ 2 (comparison) with sodium laureth sulfate (2 EO) | 9.5 | grey (initial hair color, no color absorption) | + |
| V2 | DZ 2 (comparison) with sodium laureth-5 carboxylate | 9.5 | grey (initial hair color, no color absorption) | + |
| E1 | DZ 1 (according to an exemplary embodiment of the present disclosure) with sodium laureth sulfate (2 EO) | 9.5 | dark blue | ++++ |

| Formulation | pH value | Color nuance | Color intensity |
|---|---|---|---|
| E2 DZ 1 (according to an exemplary embodiment of the present disclosure) with sodium laureth-5 carboxylate | 9.5 | bluish black | +++++ |

Color intensity:
+ = poor
+++ = medium
+++++ = very good

The formulations V1 and V2 are comparison formulations which contained the direct dye DZ 2 not according to the present disclosure (DZ 2: 3-methyl-2-(2-{4-[methyl({2-[methyl({4-[2-(3-methyl-1,3-thiazol-3-ium-2-yl)diazen-1-yl]phenyl})amino]ethyl})amino]phenyl}diazen-1-yl)-1,3-thiazol-3-ium di(methyl sulfate) (comparison)).

In the case of the coloration of V1 and V2, no color absorption could be observed, the strands were colored grey similarly to the initial hair color (Kerling, 80% greyed).

The formulations E1 and E2 are formulations according to an exemplary embodiment of the present disclosure.

When combining the dye DZ 1 with the anionic surfactant sodium laureth sulfate (2 EO) a dark blue coloration with high color intensity was observed (E1).

When combining the dye DZ 1 with the anionic surfactant sodium laureth-5 carboxylate an even more intense bluish black coloration could be attained.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for dyeing keratin fibers, the agent comprising, in a cosmetic carrier,
a) at least one direct dye of formula (I),

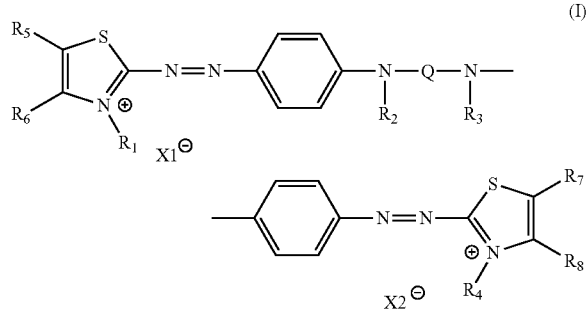

wherein
R1, R4 independently of one another stand for a $C_1$-$C_6$ alkyl group, a $C_2$-$C_6$ alkenyl group, a hydroxy $C_2$-$C_6$ alkyl group, a cyano $C_1$-$C_6$ alkyl group, a halogen $C_1$-$C_6$ alkyl group, an aryl $C_1$-$C_6$ alkyl group, a heteroaryl $C_1$-$C_6$ alkyl group, an aryl group, or a heteroaryl group, R2, R3 independently of one another stand for a hydrogen atom, a $C_1$-$C_6$ alkyl group, a $C_2$-$C_6$ alkenyl group, a hydroxy $C_2$-$C_6$ alkyl group, a cyano $C_1$-$C_6$ alkyl group, a halogen $C_1$-$C_6$ alkyl group, an aryl $C_1$-$C_6$ alkyl group, a heteroaryl $C_1$-$C_6$ alkyl group, an aryl group, or a heteroaryl group, R5, R6, R7, R8 independently of one another stand for a hydrogen atom, a $C_1$-$C_6$ alkyl group, a halogen atom from the group of chlorine, bromine, fluorine or iodine, or for a $C_1$-$C_6$ alkoxy group, X1, X2 independently of one another stand for a physiologically acceptable anion, chloride, bromide, iodide, methyl sulfate, methyl sulfonate, p-toluene sulfonate, acetate, hydrogen sulfate, ½ sulfate, or ½ tetrachlorozincate, Q stands for a grouping of the formula (III), (IV), or (V),

m, p, q each stand, independently of one another, for the numbers 2 or 3,

R9 stands for a hydrogen atom, for a $C_1$-$C_6$ alkyl group, a $C_2$-$C_6$ alkenyl group, or for a hydroxy $C_2$-$C_6$ alkyl group, and
(b) at least one anionic surfactant.

2. The agent according to claim 1, wherein the agent comprises (a) at least one direct dye of general formula (I), in which
R1, R4 independently of one another stand for a $C_1$-$C_6$ alkyl group,
R2, R3 independently of one another stand for a hydrogen atom or for a $C_1$-$C_6$ alkyl group,
R5, R6, R7, R8 each stand for a hydrogen atom.

3. The agent according to claim 1, wherein the agent comprises (a) at least one direct dye of general formula (I) selected from:
salts of 3-methyl-2-[2-(4-{[5-({4-[2-(3-methyl-1,3-thiazol-3-ium-2-yl)diazen-1-yl]phenyl}amino)pentyl]amino}phenyl)diazen-1-yl]-1,3-thiazol-3-ium,
salts of 3-methyl-2-{2-[4-({2-[2-({4-[2-(3-methyl-1,3-thiazol-3-ium-2-yl)diazen-1-yl]phenyl}amino)ethoxy]ethyl}amino)phenyl]diazen-1-yl}-1,3-thiazol-3-ium,
salts of 3-methyl-2-(2-{4-[methyl(2-{2-[methyl({4-[2-(3-methyl-1,3-thiazol-3-ium-2-yl)diazen-1-yl]phenyl})amino]ethoxy}ethyl)amino]phenyl}diazen-1-yl)-1,3-thiazol-3-ium,
salts of 2-(2-{4-[ethyl(2-{2-[ethyl({4-[2-(3-methyl-1,3-thiazol-3-ium-2-yl)diazen-1-yl]phenyl})amino]ethoxy}ethyl)amino]phenyl}diazen-1-yl)-3-methyl-1,3-thiazol-3-ium,
salts of 3-ethyl-2-{2-[4-({2-[2-({4-[2-(3-ethyl-1,3-thiazol-3-ium-2-yl)diazen-1-yl]phenyl}amino)ethoxy]ethyl}amino)phenyl]diazen-1-yl}-1,3-thiazol-3-ium, salts of 3-ethyl-2-{2-[4-({2-[2-({4-[2-(3-ethyl-1,3-thiazol-3-ium-2-yl)diazen-1-yl]phenyl}(methyl)amino)ethoxy]ethyl}(methyl)amino)phenyl]diazen-1-yl}-1,3-thiazol-3-, salts of 3-ethyl-2-(2-{4-[ethyl(2-{2-[ethyl({4-[2-(3-ethyl-1,3-thiazol-3-ium-2-yl)diazen-1-yl]phenyl})amino]ethoxy}ethyl)amino]phenyl}diazen-1-yl)-1,3-thiazol-3-ium, salts of 3-methyl-2-{2-[4-(10-{4-[2-(3-methyl-1,3-thiazol-3-ium-2-yl)diazen-1-yl]phenyl}-4J-dioxa-1,10-diazadecan-1-yl)phenyl]diazen-1-yl}-1,3-thiazol-3-ium, salts of 3-methyl-2-{2-[4-(11-{4-[2-(3-methyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium, salts of 3-methyl-2-{2-[4-(12-{4-[2-(3-methyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium, salts of 3-ethyl-2-{2-[4-(10-{4-[2-(3-ethyl-1,3-thiazol-3-ium-2-yl)diazen-1-yl]phenyl}-4J-dioxa-1,10-diazadecan-1-yl)phenyl]diazen-1-yl}-1,3-thiazol-3-ium, salts of 3-ethyl-2-{2-[4-(11-{4-[2-(3-ethyl-1,3-thiazol-3-ium-2-yl)diazen-1-yl]phenyl}-5,8-dioxa-2,11-diazadodecan-2-yl)phenyl]diazen-1-yl}-1,3-thiazol-3-ium, and salts of 3-ethyl-2-{2-[4-(12-{4-[2-(3-ethyl-1,3-thiazol-3-ium-2-yl)diazen-1-yl]phenyl}-6,9-dioxa-3,12-diazatetradecan-3-yl)phenyl]diazen-1-yl}-1,3-thiazol-3-ium.

4. The agent according to claim 1, wherein the agent comprises, in relation to the total weight of the agent, one or more direct dyes (a) of formula (I) in a total amount of from about 0.01 to about 4.5% by weight.

5. The agent according to claim 1, wherein the agent comprises (b) at least one anionic surfactant selected from:
linear and branched fatty acids having 8 to 30 C atoms,
ether carboxylic acids of formula R—O—($CH_2$—$CH_2$O)$_x$—$CH_2$—COOM, in which
R stands for a linear alkyl group having 8 to 30 C atoms,
x stands for an integer from 0 to 16,
M stands for hydrogen, a metal, an alkali metal, sodium, potassium, lithium, an alkaline earth metal, magnesium, calcium, zinc, or an ammonium ion ($NH_4^+$),
acyl sarcosides having 8 to 24 C atoms in the acyl group,
acyl taurides having 8 to 24 C atoms in the acyl group,
acyl isethionates having 8 to 24 C atoms in the acyl group, which are accessible by esterification of $C_8$-$C_{24}$ fatty acids with the sodium salt of the 2-hydroxyethane sulfonic acid (isethionic acid),
amide ether carboxylic acids, $R^1$—CO—$NR^2$—$CH_2CH_2$—O—($CH_2CH_2O$)$_y$$CH_2$COOM, wherein
$R^1$ stands for a C2-C30 alkyl group,
y stands for an integer from 1 to 20,
$R^2$ stands for hydrogen, a methyl, ethyl, propyl, isopropyl, n-butyl, t-butyl or iso-butyl group, and
M stands for hydrogen, a metal, an alkali metal, sodium, potassium, lithium, an alkaline earth metal, magnesium, calcium, zinc, or an ammonium ion ($NH_4^+$).

6. The agent according to claim 1, wherein the agent comprises, as anionic surfactant, (b) at least one ether carboxylic acid of formula (B1)

R—O—(CH2-CH2O)x-CH2-COOM     (B1)

wherein
R stands for a linear alkyl group having 8 to 30 C atoms,
x stands for an integer from 0 to 16,
M stands for hydrogen, a metal, an alkali metal, sodium, potassium, lithium, an alkaline earth metal, ½ magnesium, ½ calcium, ½ zinc, or an ammonium ion ($NH_4^+$).

7. The agent according to claim 1, wherein the agent comprises, in relation to the total weight of the agent, one or more anionic surfactants (b) in a total amount of from about 0.05 to about 4.5% by weight.

8. The agent according to claim 6, wherein the ratio by weight of all anionic surfactants of formula (B1) contained in the agent to the total amount of the anionic surfactants contained in the agent lies at a value of about 0.5 to about 0.9.

* * * * *